(12) United States Patent
Anavi-Goffer et al.

(10) Patent No.: US 11,612,572 B2
(45) Date of Patent: Mar. 28, 2023

(54) TREATMENT OF SCHIZOPHRENIA USING BETA-CARYOPHYLLENE AND CB2 RECEPTOR AGONISTS

(71) Applicant: Sharon Anavi-Goffer, Oranit (IL)

(72) Inventors: Sharon Anavi-Goffer, Oranit (IL); Juerg Gertsch, Schaffhausen (CH)

(*) Notice: Subject to any disclaimer, the term of this patent is extended or adjusted under 35 U.S.C. 154(b) by 0 days.

(21) Appl. No.: 16/869,672

(22) Filed: May 8, 2020

(65) Prior Publication Data

US 2020/0261374 A1 Aug. 20, 2020

Related U.S. Application Data

(63) Continuation of application No. 15/432,198, filed on Feb. 14, 2017, now abandoned, which is a
(Continued)

(51) Int. Cl.
| | |
|---|---|
| *A61K 31/015* | (2006.01) |
| *A61P 25/18* | (2006.01) |
| *A61K 31/5513* | (2006.01) |
| *A61K 31/5415* | (2006.01) |
| *A61K 31/4515* | (2006.01) |
| *A61K 31/519* | (2006.01) |
| *A61K 45/06* | (2006.01) |

(Continued)

(52) U.S. Cl.
CPC .......... *A61K 31/015* (2013.01); *A61K 9/0019* (2013.01); *A61K 9/0053* (2013.01); *A61K 31/4515* (2013.01); *A61K 31/519* (2013.01); *A61K 31/5415* (2013.01); *A61K 31/5513* (2013.01); *A61K 45/06* (2013.01); *A61K 47/20* (2013.01); *A61P 25/18* (2018.01)

(58) Field of Classification Search
CPC .............................. A61K 31/015; A61P 25/18
USPC .................................................. 514/766, 720
See application file for complete search history.

(56) References Cited

U.S. PATENT DOCUMENTS

2007/0154534 A1* 7/2007 Sheitman ............. A61K 9/0019
424/449
2007/0219229 A1* 9/2007 Eatherton ............... A61P 19/10
514/300

(Continued)

FOREIGN PATENT DOCUMENTS

KR 20110073653 A 6/2011
WO WO-2006017892 A1 2/2006

(Continued)

OTHER PUBLICATIONS

Gertsch et al. "Beta-caryophyllene is a dietary cannabinoid," PNAS, 2008, vol. 105, No. 26, pp. 9099-9104 (Year: 2008).*

(Continued)

*Primary Examiner* — Shengjun Wang
(74) *Attorney, Agent, or Firm* — Eversheds Sutherland (US) LLP

(57) ABSTRACT

Disclosed are compositions comprising beta-caryophyllene (BCP) for use in the treatment of schizophrenia, methods of making such compositions and methods of treating schizophrenia using BCP. Disclosed are also compositions comprising CB2 receptor agonists for use in the treatment of schizophrenia, methods of making such compositions and methods of treating schizophrenia using CB2 receptor agonists.

10 Claims, 38 Drawing Sheets

Related U.S. Application Data continuation of application No. 14/385,739, filed as application No. PCT/IB2013/052182 on Mar. 19, 2013, now abandoned.

(60) Provisional application No. 61/612,411, filed on Mar. 19, 2012.

(51) Int. Cl.
*A61K 9/00* (2006.01)
*A61K 47/20* (2006.01)

(56) References Cited

U.S. PATENT DOCUMENTS

| | | | |
|---|---|---|---|
| 2008/0234259 | A1* | 9/2008 | Muthuppalaniappan ................ C07D 231/54 514/232.8 |
| 2015/0051299 | A1 | 2/2015 | Anavi-Goffer et al. |
| 2016/0089349 | A1 | 3/2016 | Anavi-Goffer et al. |

FOREIGN PATENT DOCUMENTS

| | | | | |
|---|---|---|---|---|
| WO | WO-2006037194 | A1 * | 4/2006 | ............ A61P 29/00 |
| WO | WO-2013140342 | A1 | 9/2013 | |
| WO | WO-2018060766 | A2 | 4/2018 | |
| WO | WO-2018112138 | A1 | 6/2018 | |

OTHER PUBLICATIONS

Meyer et al. "Inflammatory processes in schizophrenia: A promising neuroimmunological target for the treatment of negative/cognitive symptoms and beyond," Pharmacology & Therapeutics, 2011, vol. 132, pp. 96-110. (Year: 2011).*
Morera et al. "Acute phaser proteins as biological markers of negative psychopathology in paranoid schizophrenia," Acta Espanolas de Psiquiatria, 2007, vol. 35, No. 4, pp. 249-252 (Year: 2007).*
Kelava et al. "Biological Action of Drug Solvent,". Periodicum Biologorum, 2011, vol. 113, No. 3, pp. 311-320 (Year: 2011).*
Bosier, et al., Revising the complex influences of cannabinoids on motor functions unravels pharmacodynamic differences between cannabinoid agents, Neuropharmacology, 59(6):503-510 (Nov. 2010).
Ceci, et al., Interaction Between the Endocannabinoid and Serotonergic System in the Exhibition of Head Twitch Response in Four Mouse Strains, Neurotoxicity Research, 27(3):275-283 (Apr. 2015).
Fecthner, et al., Role of cannabinoid receptor 2 in mediating interleukin-1 B-induced inflammation in rheumatoid arthritis synovial fibroblasts, Clinical and Experimental Rheumatology, 37(6):1026-1035 (2019) Abstract Only.
Frydecka, et al., Interleukin-6: the missing element of the neurocognitive deterioration in schizophrenia? The focus on genetic underpinnings, cognitive impairment and clinical manifestation, European Archives of Psychiatry and Clinical Neuroscience, 265(6):449-459 (Sep. 2015).
Geng, et al., Inhibition of titanium-particle-induced inflammatory osteolysis through inactivation of cannabinoid receptor 2 by AM630, Journal of Biomedical Materials Research Part A, 95(1):321-326 (Oct. 2010).
Gertsch et al., Methylhonokiol attenuates neuroinflammation: a role for cannabinoid receptors?, Journal of Neuroinflammation, 9(1):1-5 (Dec. 2012).
Halberstadt, et al., Serotonergic hallucinogens as translational models relevant to schizophrenia, International Journal of Neuropsychopharmacology, 16(10):2165-2180 (Nov. 2013).
Hanus, et al., HU-308: A Specific agonist for $CB_2$, a peripheral cannabinoid receptor, Proceedings of the National Academy of Sciences, 96(25):14228-14233 (Dec. 1999).
Hartwig, et al., Inflammatory Biomarkers and Risk of Schizophrenia A 2-Sample Mendelian Randomization Study, JAMA Psychiatry, 74(12):1226-1233 (Dec. 2017).
Henriquez, et al., Δ9-tetrahydrocannabinol (THC) impairs CD8+ T cell-mediated activation of astrocytes, J. Neuroimmune Pharmacol., 15(4):863-874 (Dec. 2020).
International Search Report & Written Opinion dated Jul. 18, 2013 in Int'l PCT Patent Appl. Serial No. PCT/IB2013/052182.
Ishiguro, et al., Brain Cannabinoid CB2 Receptor in Schizophrenia, Biological Psychiatry, 67(10):974-82 (May 2010).
Kim, et al., The New 4-O-Methylhonokiol Analog GS12021 Inhibits Inflammation and Macrophage Chemotaxis: Role of AMP-Activated Protein Kinase a Activation, PLos ONE, 10:1-19 (2015).
Kruk-Slomka, et al., The Impact of CB2 Receptor Ligands on the MK-801-Induced Hyperactivity in Mice, Neurotoxicity Research, 31 (3):410-420 (Apr. 2017).
Lee, Inhibitory effect of 4-O-methylhonokiol on lipopolysaccharide-induced neuroinflammation, amyloidogenesis and memory impairment via inhibition of nuclear factor-kappaB in vitro and in vivo models, Journal of Neuroinflammation, 9(1):1-9 (2012).
Martin, et al., Chronic LSD alters gene expression in the mPFC relevant to schizophrenia, Neuropharmacology, 83:1-8 (Aug. 2014).
Martino, et al., What Does Immunology Have to Do With Normal Brain Development and the Pathophysiology Underlying Tourette Syndrome and Related Neuropsychiatric Disorders?, Frontiers in Neurology, 16:1101, pp. 1-27 (Sep. 2020).
McNaught, et al., Advances in Understanding and Treatment of Tourette Syndrome, Nature Review Neurology, 7(12):667-676 (Dec. 2011).
Naudin, et al., A differential role for interleukin-6 and tumor necrosis factor-a in schizophrenia?, Schizophrenia Research, 26(2-3):227-233 (Aug. 1997).
Roche, et al., Brain $CB_2$ Receptors: Implications for Neuropsychiatric Disorders, Pharmaceuticals, 3(8):2517-2553 (Aug. 2010).
Schuehly, et al., Mechanisms of Osteoclastogenesis Inhibition by a Novel Class of Biphenyl-Type Cannabinoid $CB_2$ Receptor Inverse Agonists, Chemistry & Biology, 18(8):1053-1064 (Aug. 2011).
Soethoudt, et al., Cannabinoid $CB_2$ receptor ligand profiling reveals biased signalling and off-target activity, Nature Communications, 8(1):1-4 (Jan. 2017).
Umezu, et al., Ambulation-promoting effect of peppermint oil and identification of its active constituents, Pharmacology Biochemistry and Behavior, 69(3-4):383-390 (Jul. 2001).
Xu, et al., Anti-inflammatory property of the cannabinoid receptor-2-selective agonist JWH-133 in a rodent model of autoimmune uveoretinitis, Journal of Leukocyte Biology, 82(3):532-541 (Sep. 2007).
Anavi-Goffer, et al., Modulation of L-α-Lysophosphatidylinositol/GPR55 Mitogen-activated Protein Kinase (MAPK) Signaling by Cannabinoids, Journal of Biological Chemistry, 287(1):91-104 (Jan. 2012).

* cited by examiner

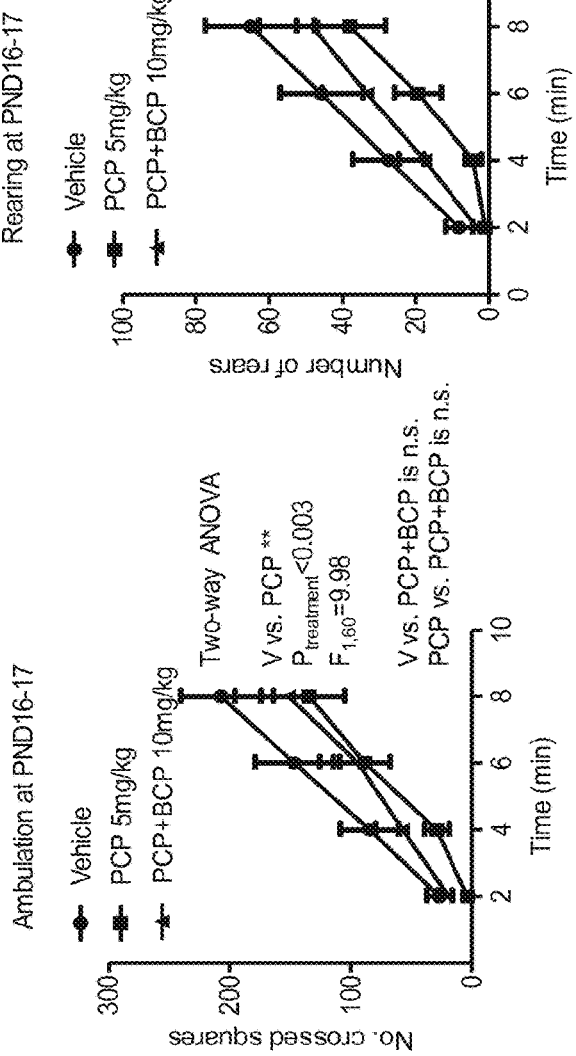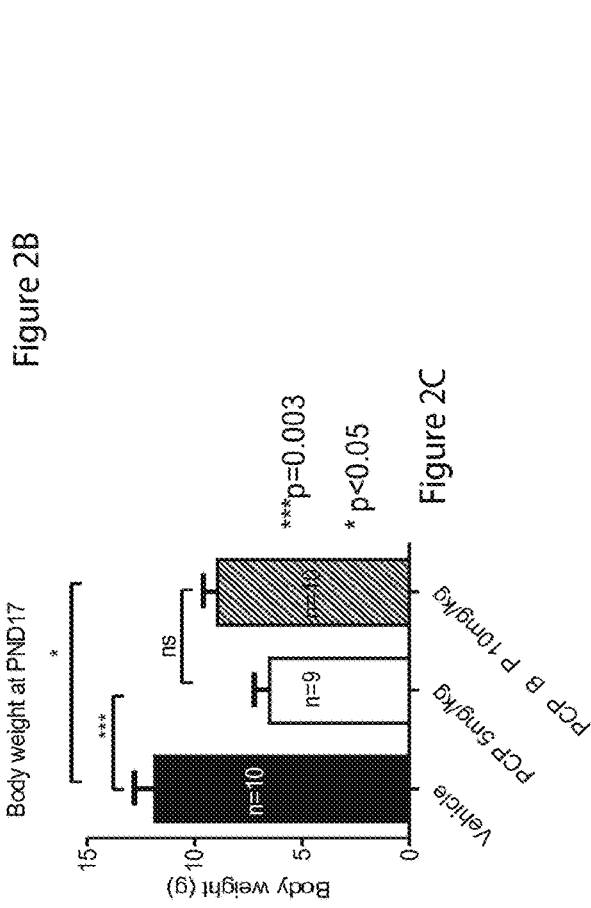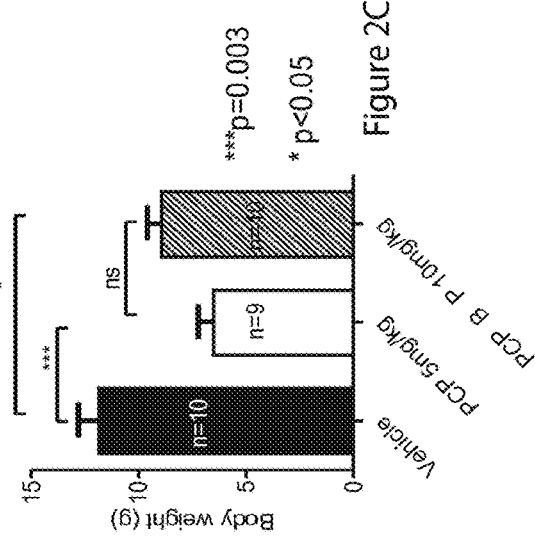
Figure 2A
Figure 2B
Figure 2C

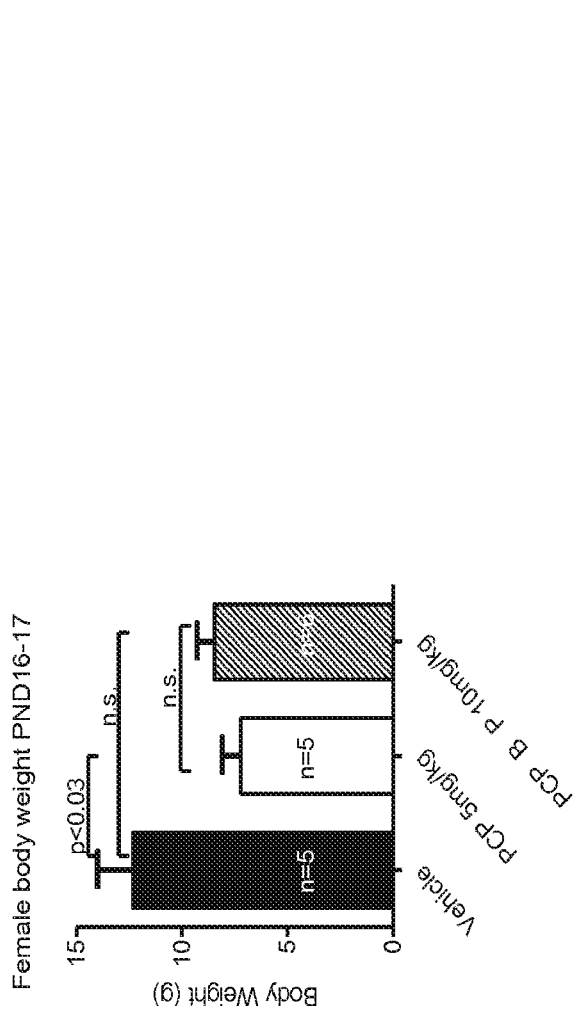
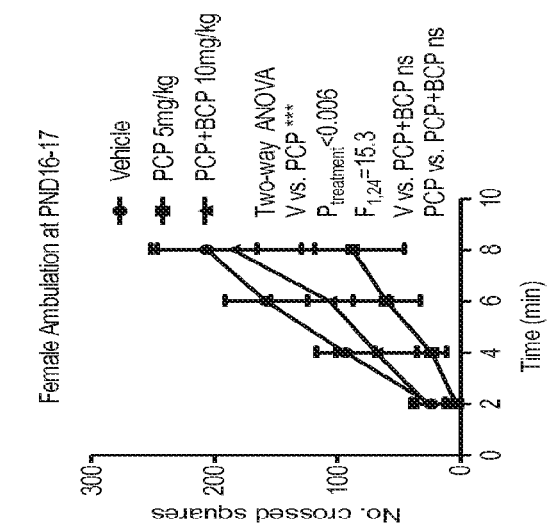
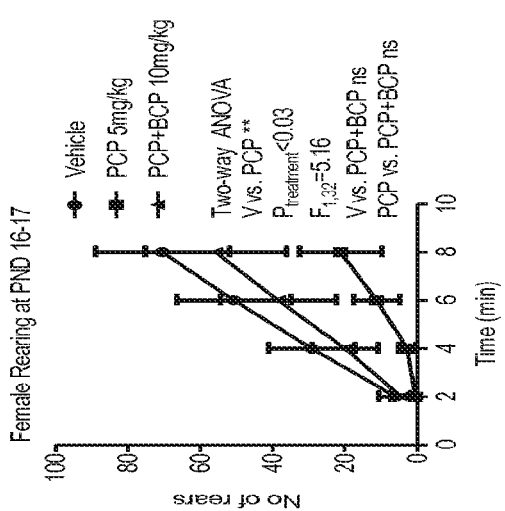
Figure 3D
Figure 3E
Figure 3F

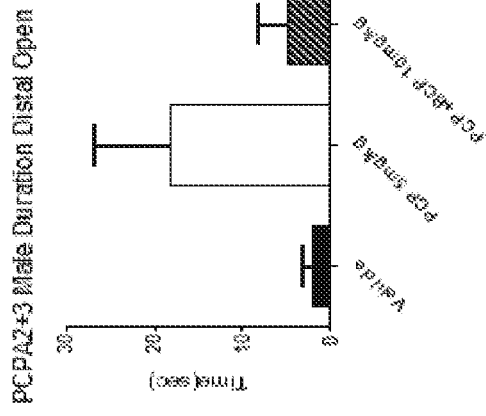
Figure 6F
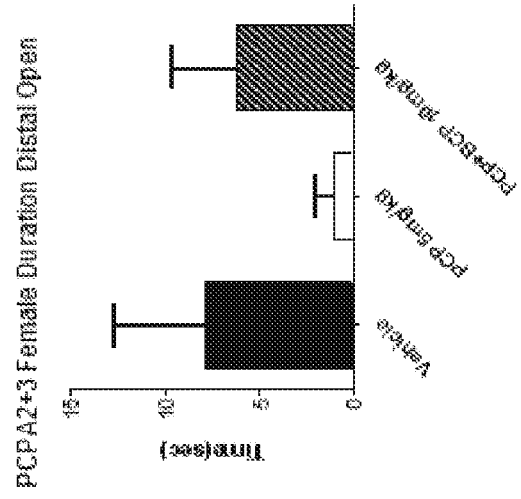
Figure 6E
Figure 6H
Figure 6G

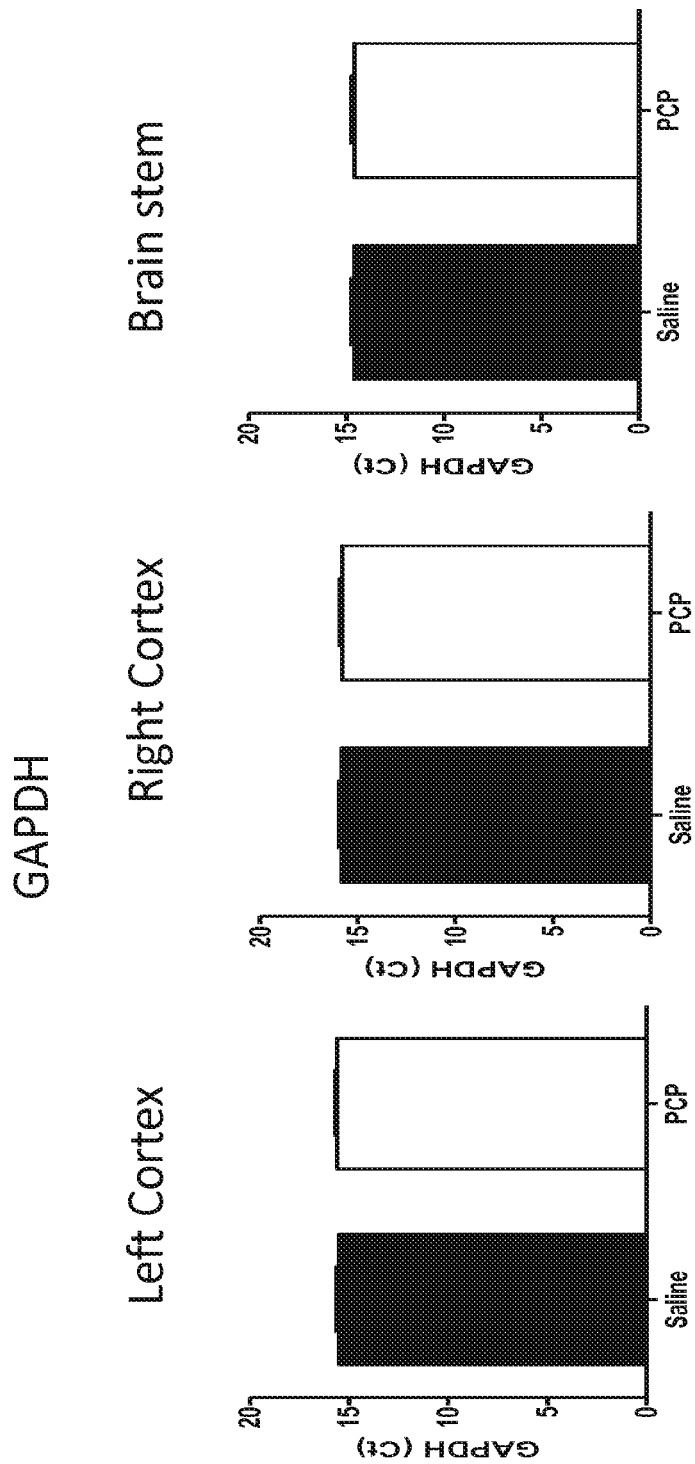

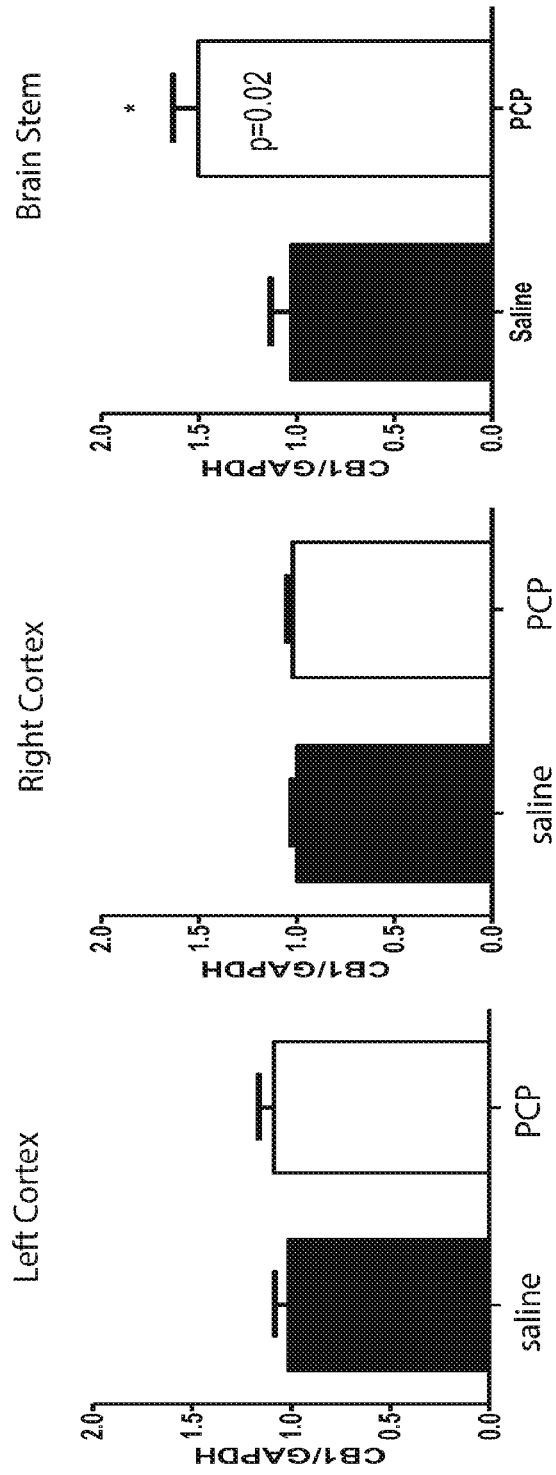

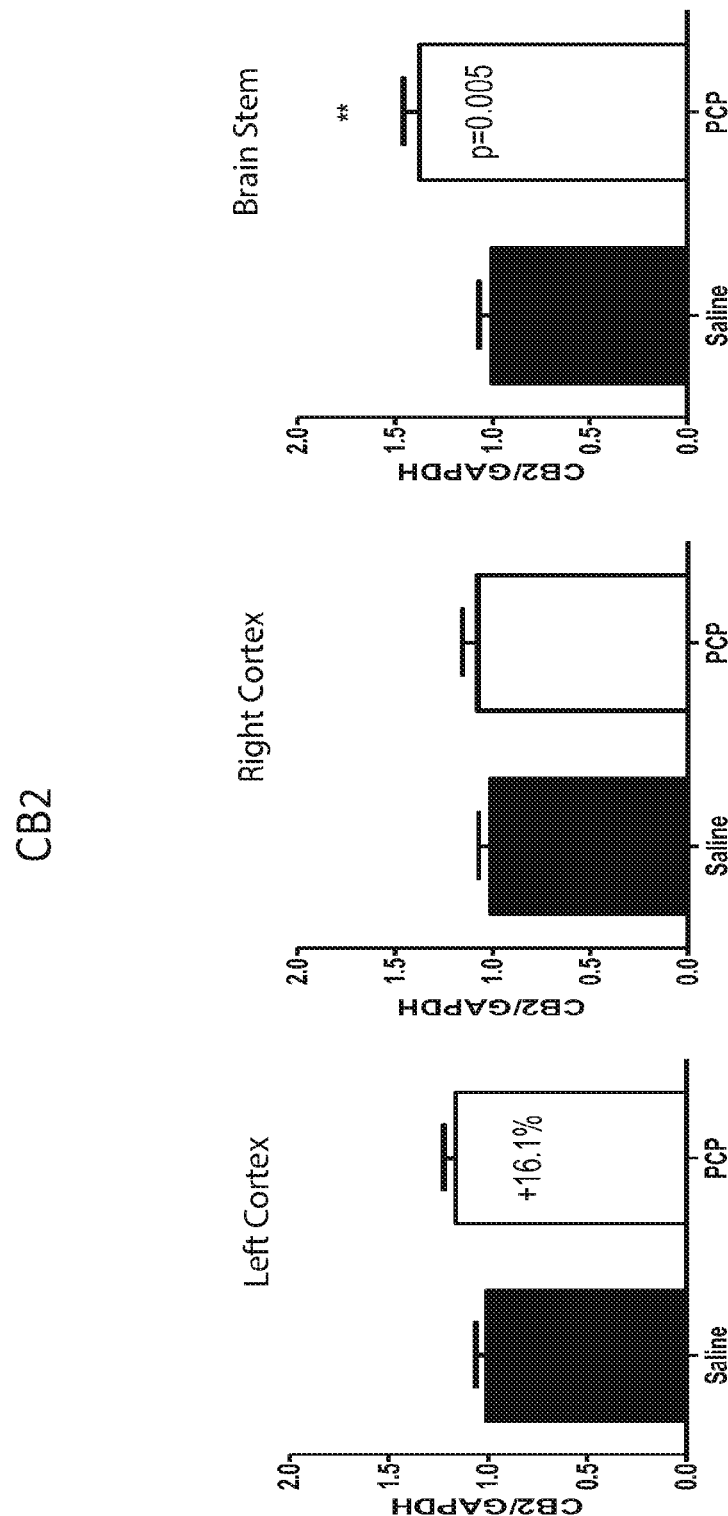

(−) A reduction in expression in PCP-treated mice compared with control (vehicle-treated) animals.
(+) An increase in expression in PCP-treated mice compared with control (vehicle-treated) animals.

|  | Left cortex | Right cortex | Basal ganglia | Brain stem |
|---|---|---|---|---|
| CB1 | −17% | ns | −36% $p=0.07$ | −32% $p<0.001$ |
| CB2 ~50kDa | −17% | ns | −14% | −23% $p<0.05$ |
| 'CB2 complexes' 64 kDa | Signal too low to detect | +87% $p<0.001$ | +74% | −23% $p=0.051$ |

Figure 8

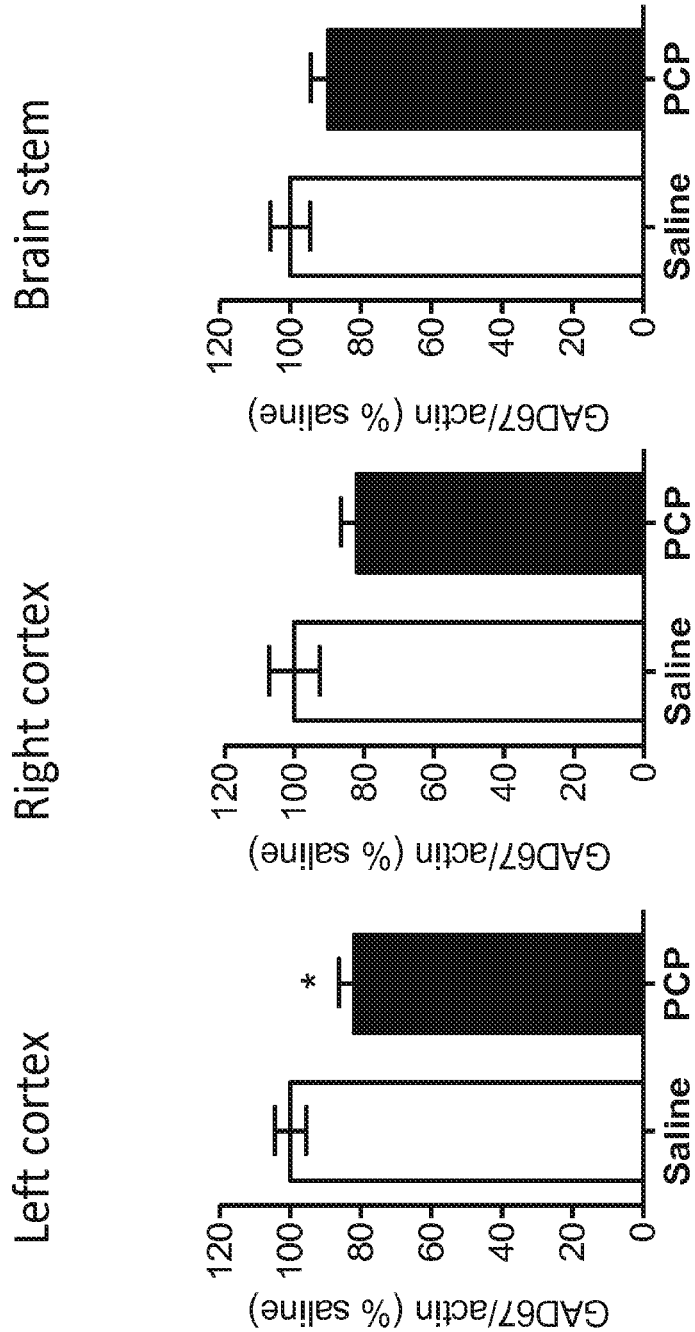

| Endocannabinoids | Ligand | Affinity (Ki, nM) | | Selectivity | Efficacy (Emax, %) | | | Potency (EC$_{50}$, nM) | | |
|---|---|---|---|---|---|---|---|---|---|---|
| | | CB$_1$ | CB$_2$ | | CB$_1$ | CB$_2$ | GPR55 | CB$_1$ | CB$_2$ | GPR55 |
| 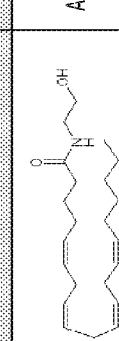 | Anandamide | 90-543 | 370-2000 | 3 | 30-100/ 66 | 38-64/ 58 | 73 | 80-200/30 | >1000/ 27 | 18 |
| 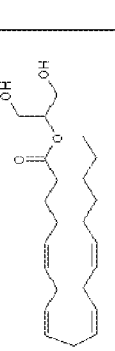 | 2-AG | 58-470 | 145-1400 | 3 | 80/92 | 60/ 87 | 99 | 430/520 | 780/ 620 | 3 |
Figure 11B

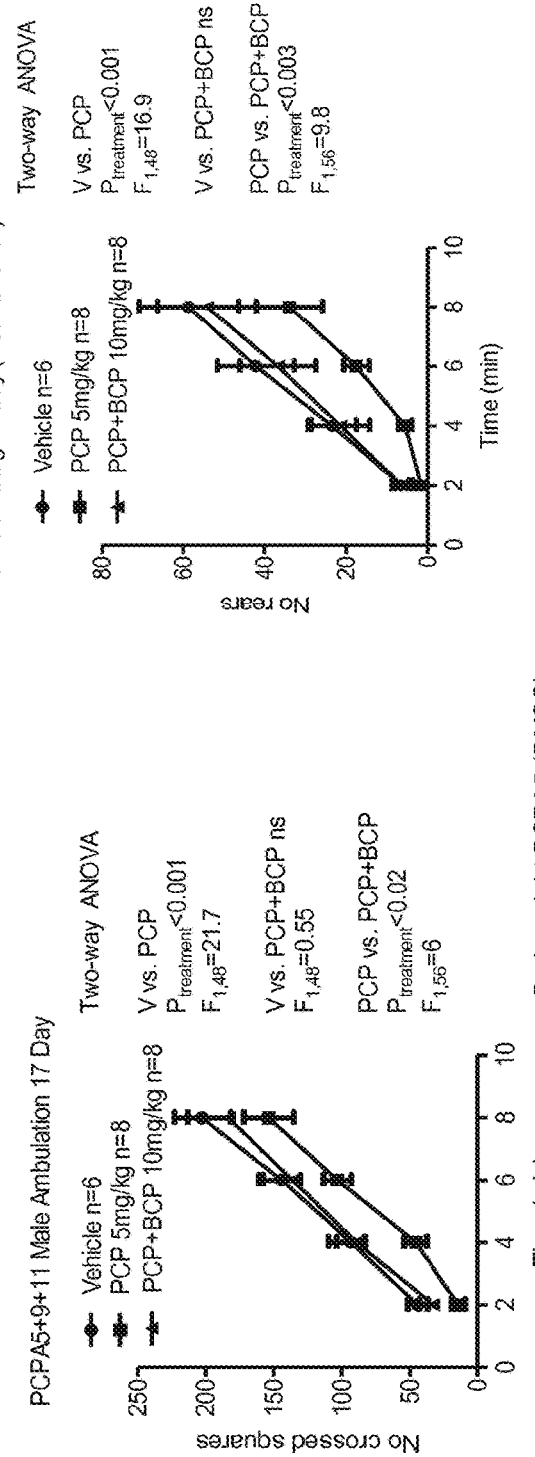
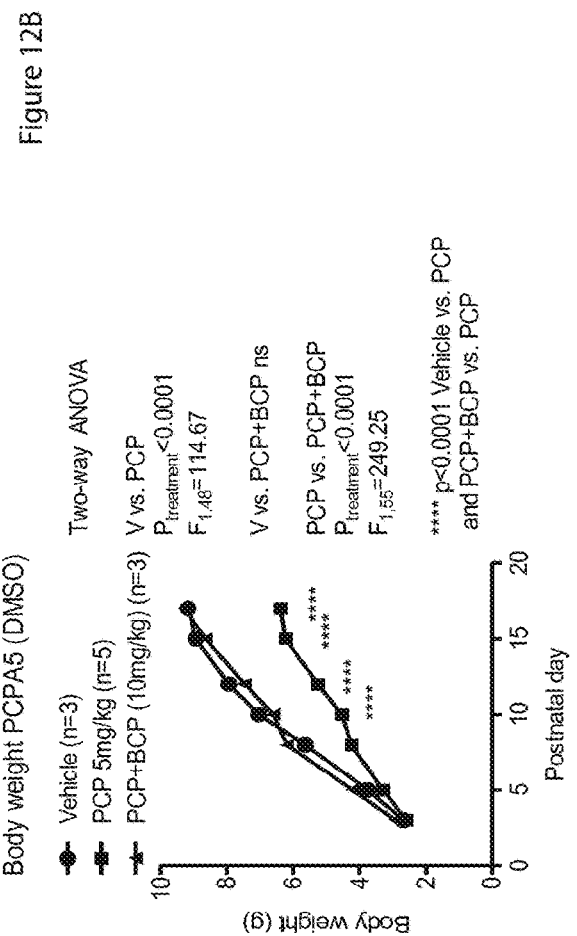
Figure 12A
Figure 12B
Figure 12C

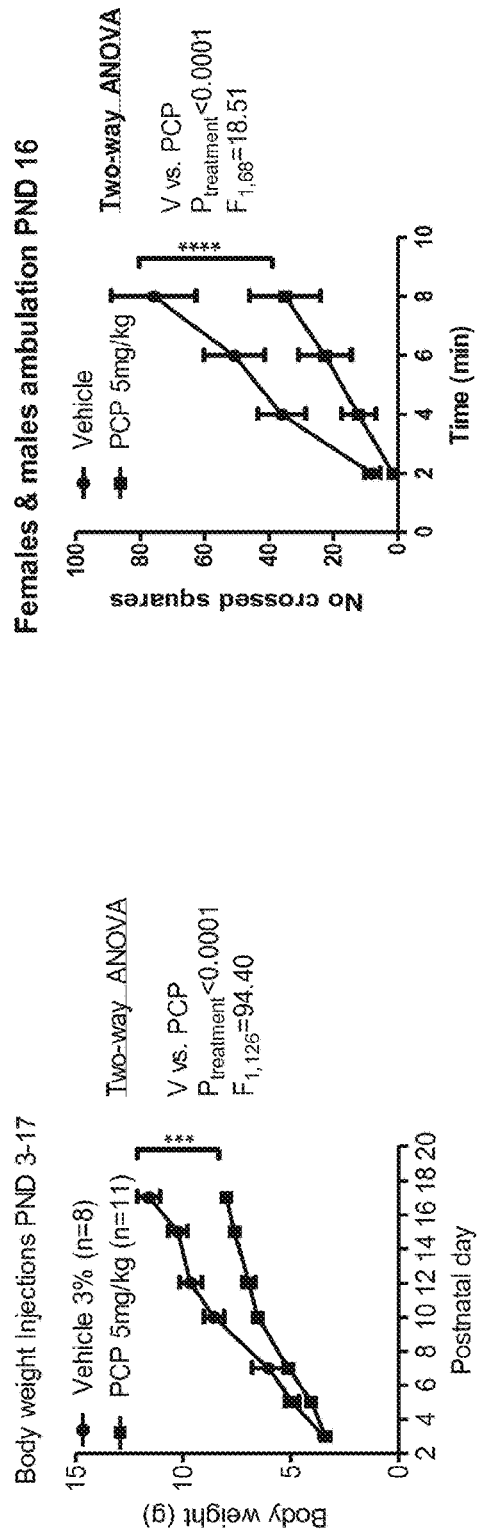
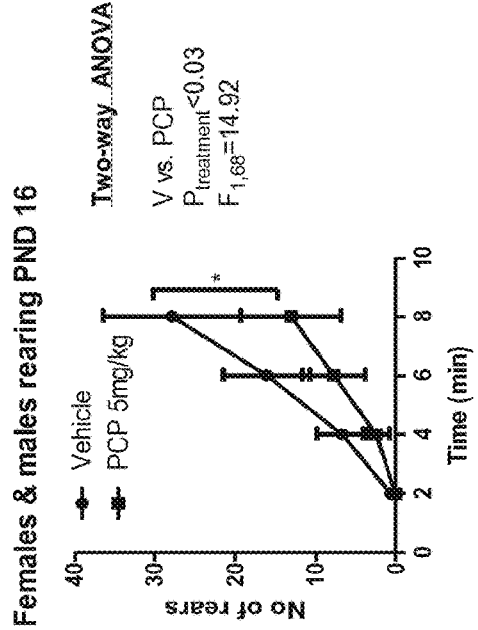
Figure 13A
Figure 13B
Figure 13C

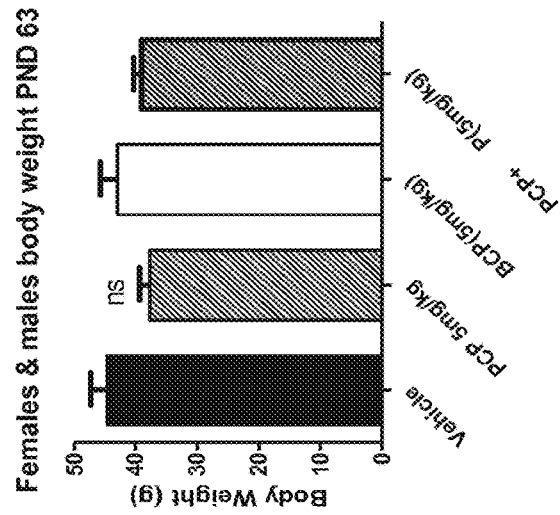
Figure 14A
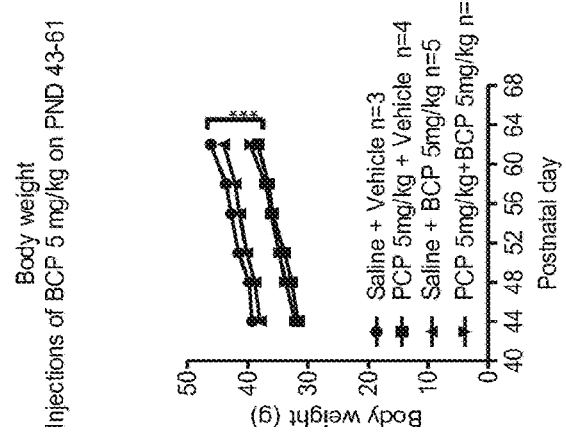
Figure 14C
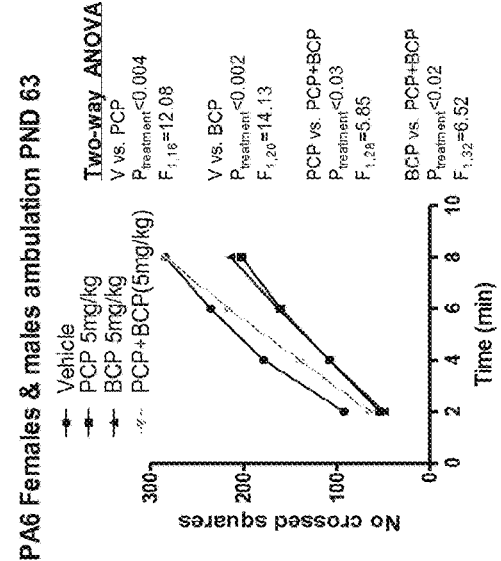
Figure 14B
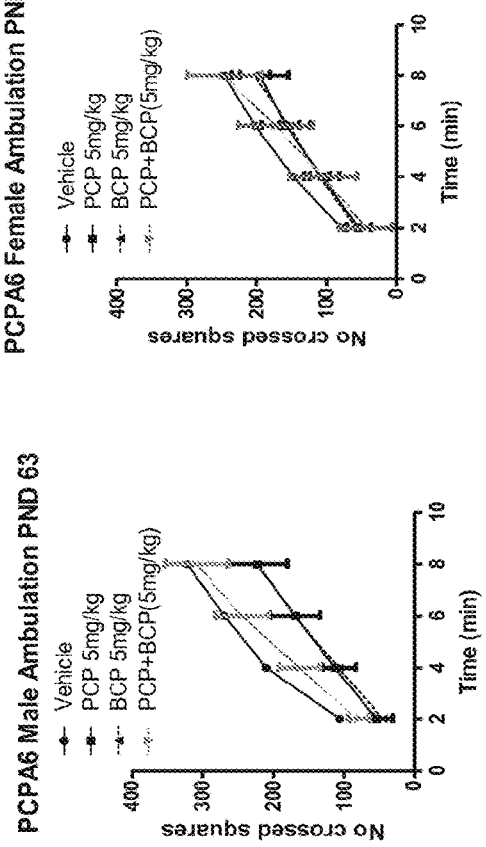
Figure 14D
Figure 14E

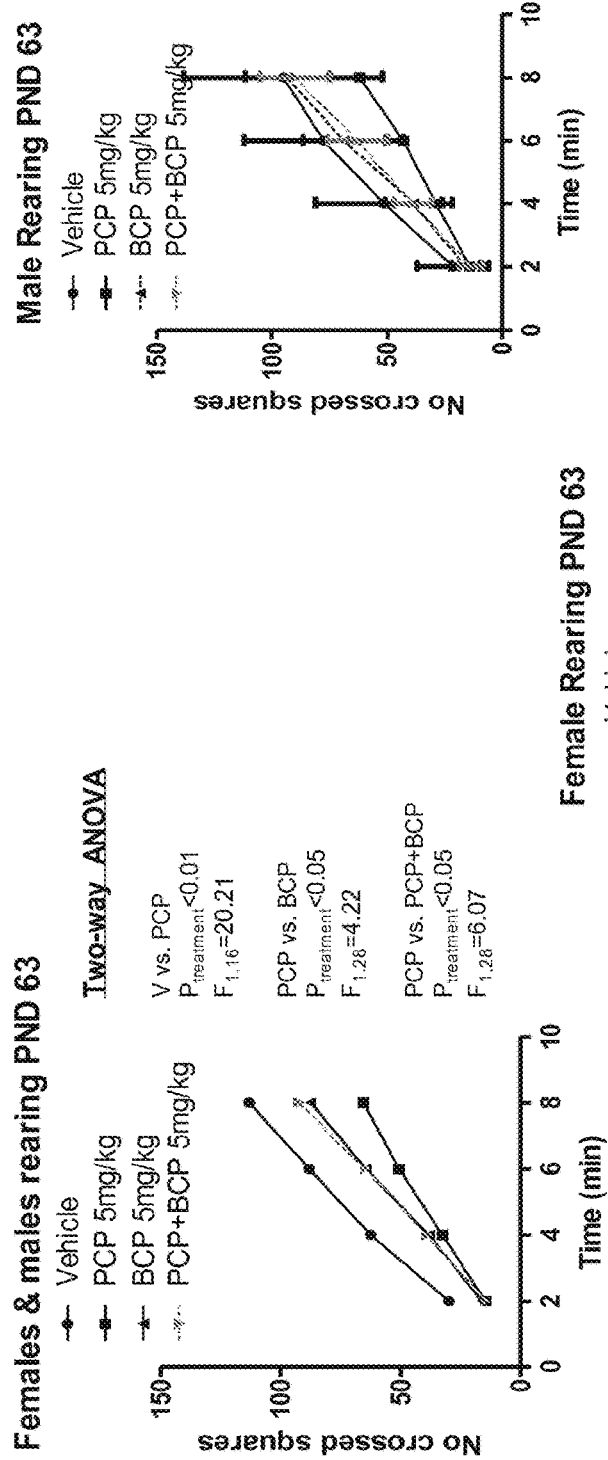
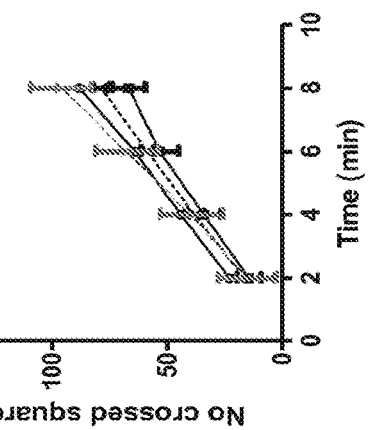
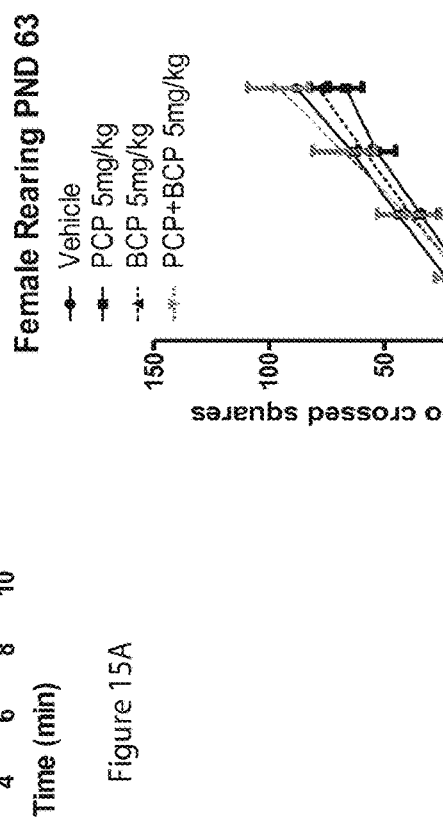
Figure 15A
Figure 15B
Figure 15C

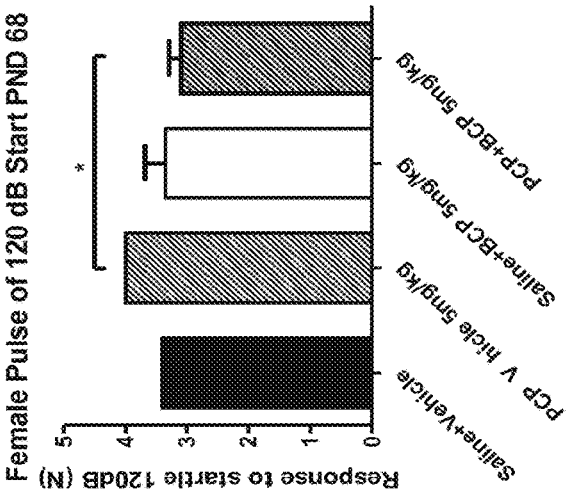
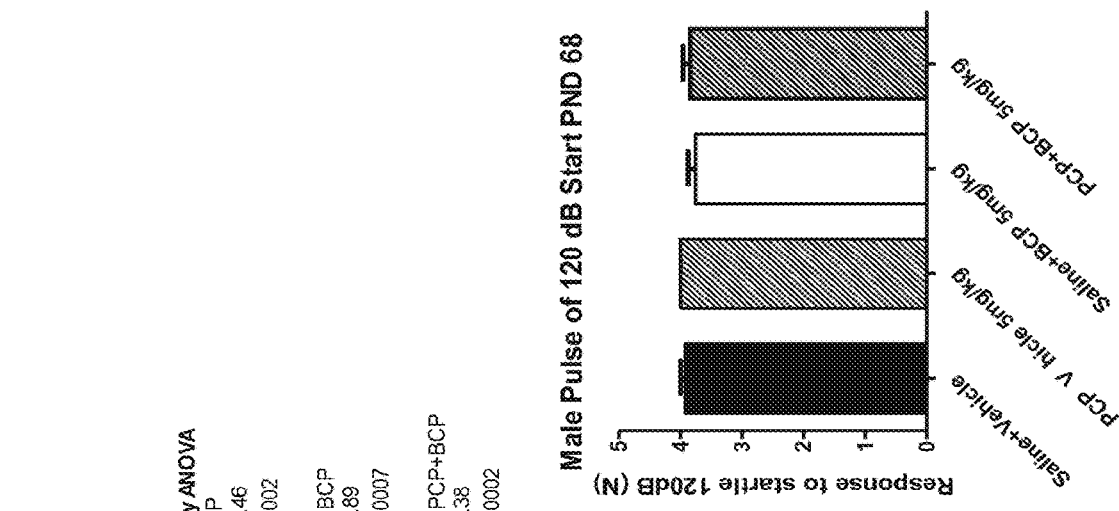
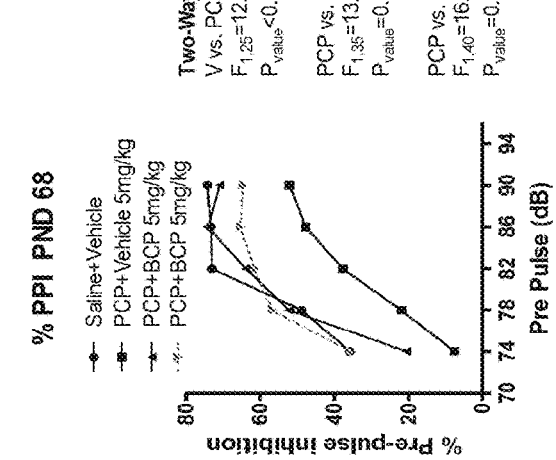
Figure 16A
Figure 16B
Figure 16C

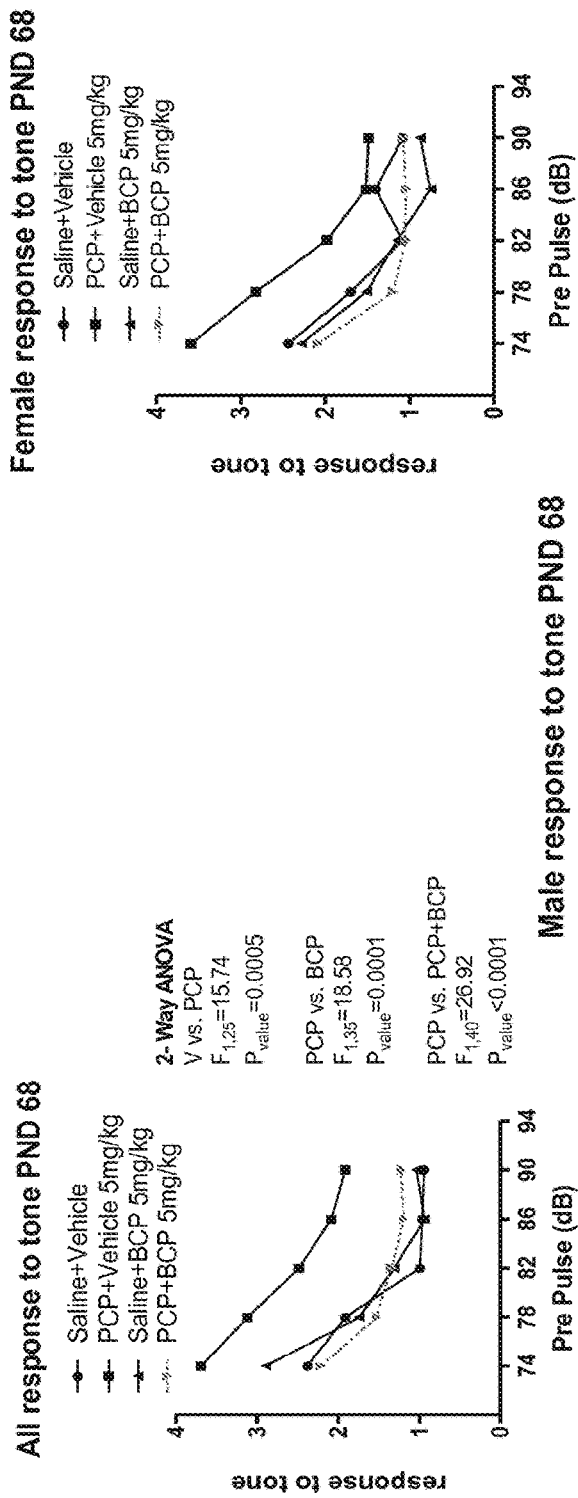
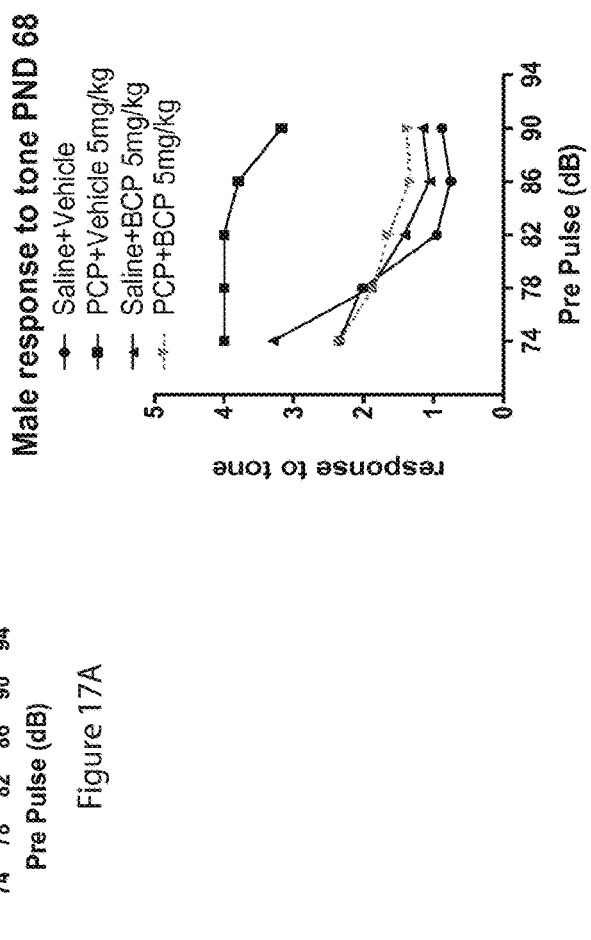
Figure 17A
Figure 17B
Figure 17C

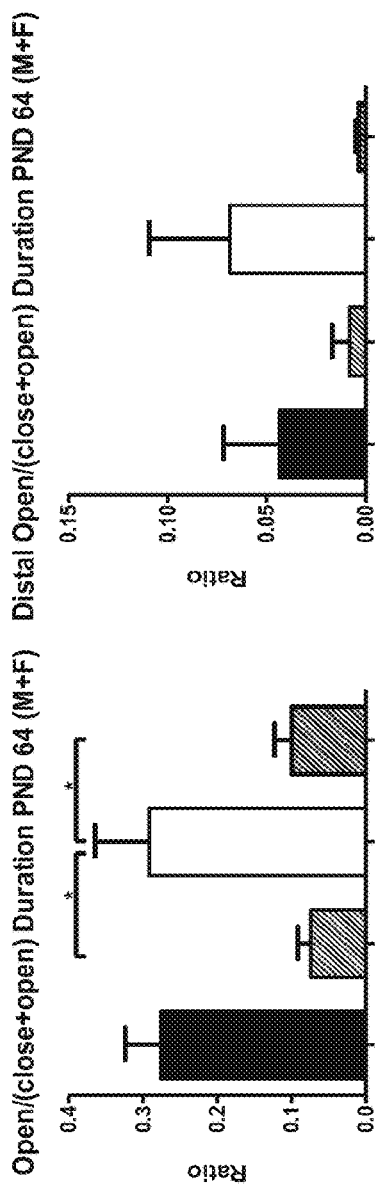
Figure 19A
Figure 19B
Figure 19C
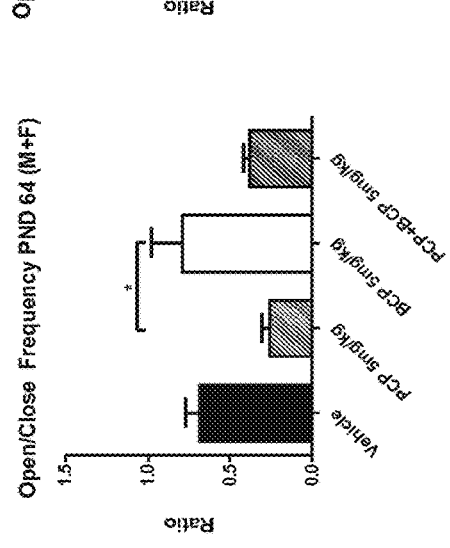
Figure 19D
Figure 19E
Figure 19F

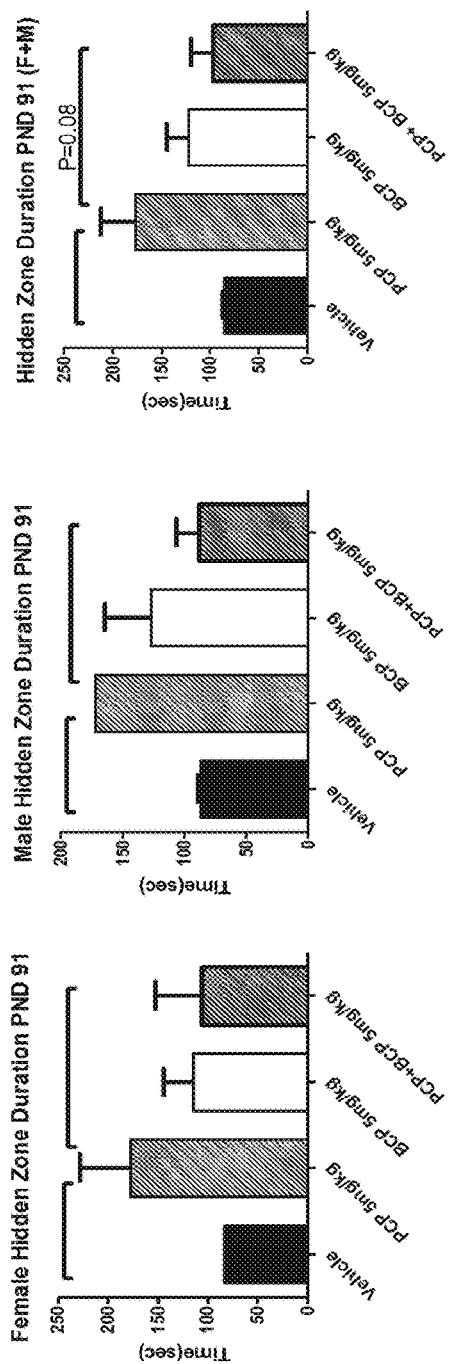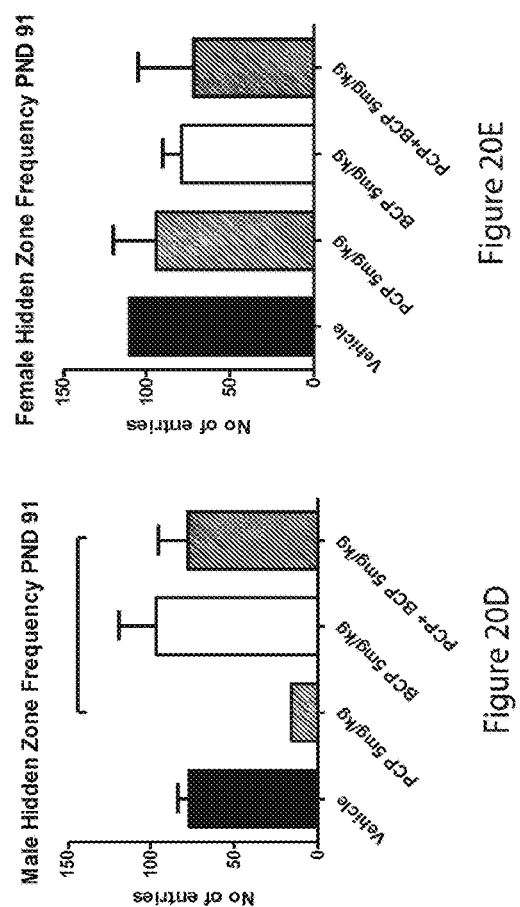
Figure 20A Figure 20B Figure 20C Figure 20D Figure 20E

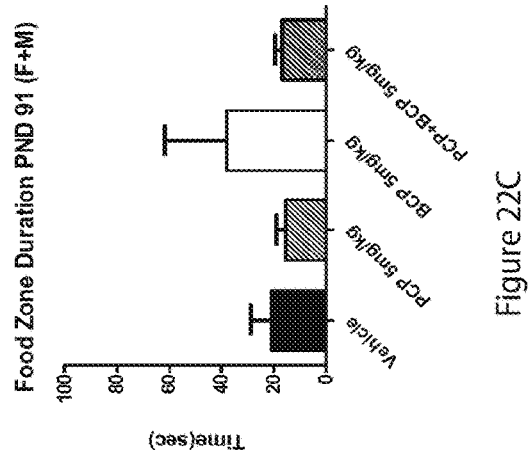
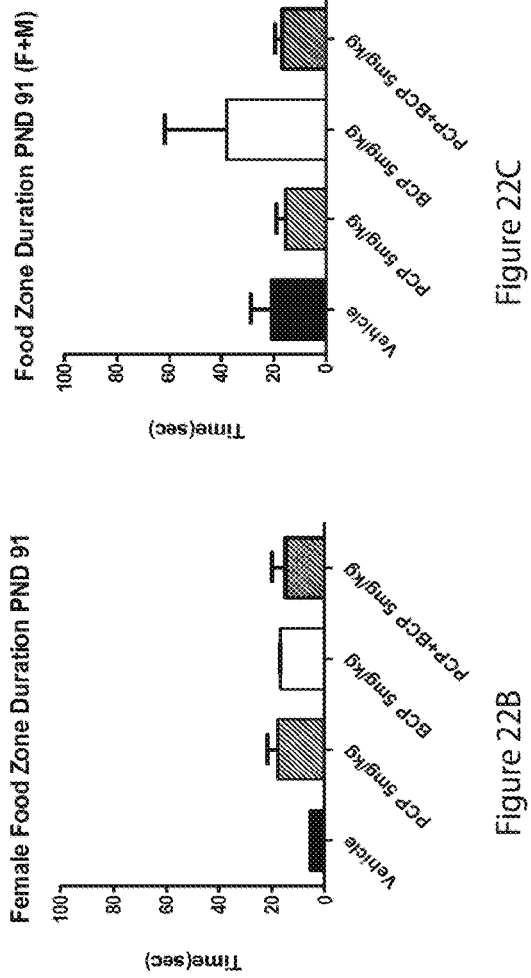
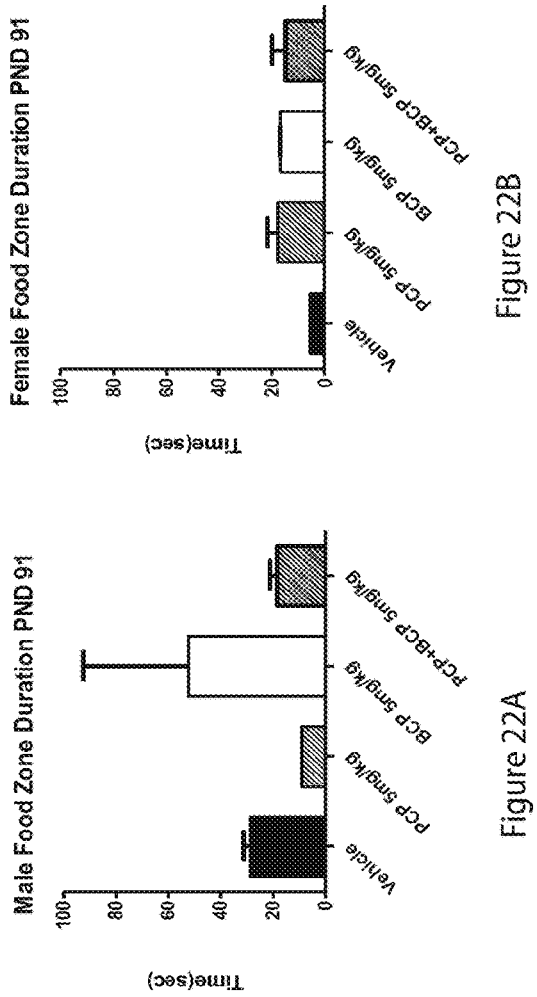
Figure 22A
Figure 22B
Figure 22C
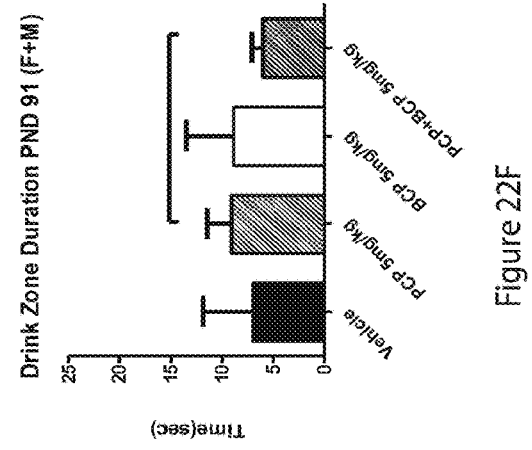
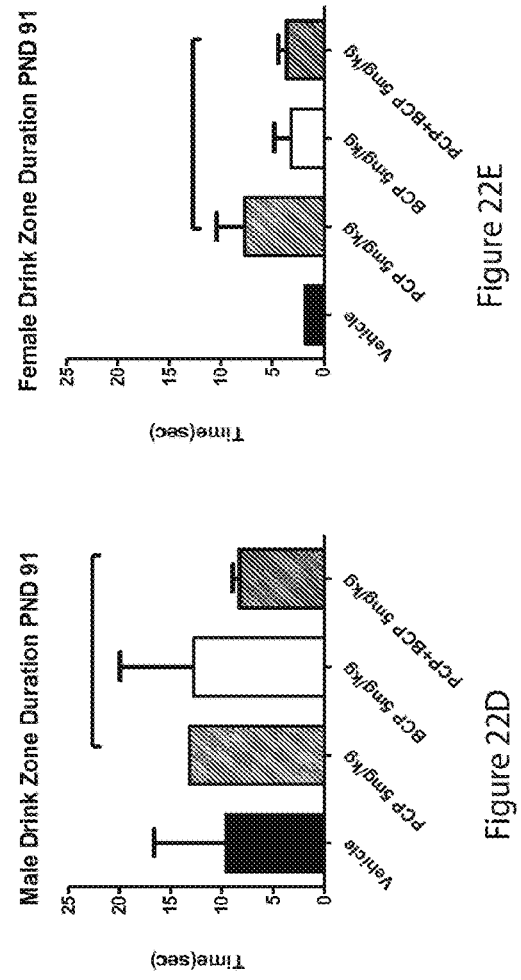
Figure 22D
Figure 22E
Figure 22F

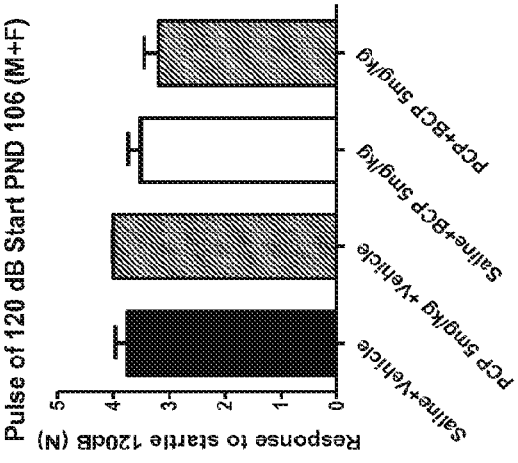
Figure 25A  Figure 25B  Figure 25C
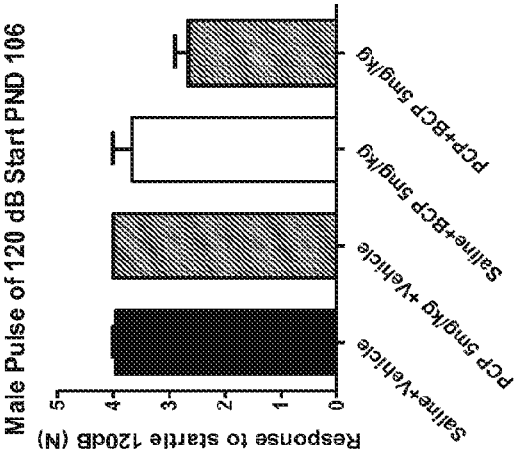
Figure 25D  Figure 25E  Figure 25F
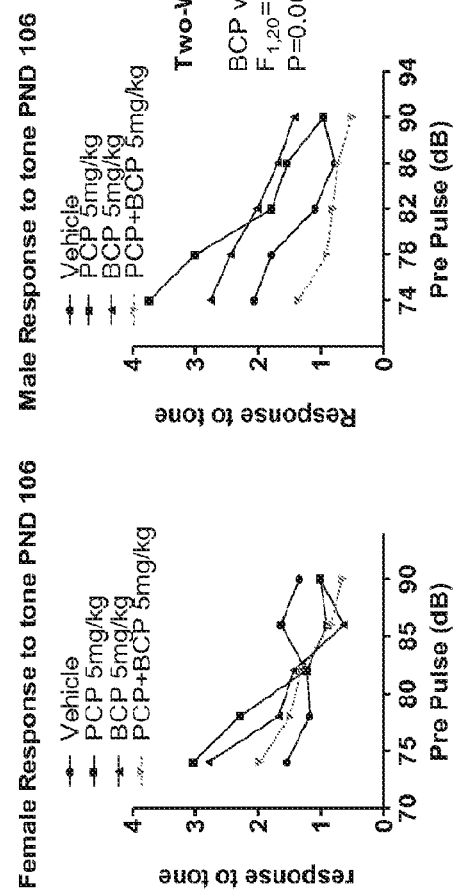

TREATMENT OF SCHIZOPHRENIA USING BETA-CARYOPHYLLENE AND CB2 RECEPTOR AGONISTS

RELATED APPLICATION

This application is a continuation of U.S. application No. 15/432,198, filed Feb. 14, 2017, which is a continuation of U.S. application No. 14/385,739, filed Sep. 16, 2014, which is a 35 U.S.C. § 371 national stage application of International Patent Application Ser. No. PCT/IB2013/052182, filed on Mar. 19, 2013, which claims priority to U.S. Provisional Patent Application Serial No. 61/612,411, filed on Mar. 19, 2012, the entire contents of each of which are incorporated by reference in their entireties.

FIELD AND BACKGROUND OF THE INVENTION

The invention, in some embodiments, relates to the field of therapy and more particularly, but not exclusively, to compositions comprising beta-caryophyllene (BCP), methods of making the compositions and methods using BCP, for the treatment of schizophrenia. The invention, in some embodiments, relates to the field of therapy and more particularly, but not exclusively, to compositions comprising Cannabinoid Receptor Type 2 (CB2) receptor agonists, methods of making the compositions and methods using CB2 receptor agonists for the treatment of schizophrenia.

Schizophrenia affects about 1% of the population (Lewis & Lieberman, 2000), and genetic and environmental factors underlie the eventual eruption of the disease (Ross, 2006). Schizophrenia is often chronic, characterized by deterioration of social contact, cognitive deficits, anxiety and depression, resulting in suicide in about 10% of the schizophrenic population (Lewis & Lieberman, 2000).

Different subtypes of schizophrenia are defined according to the most significant and predominant characteristics present, as follows: Paranoid schizophrenia; Disorganized schizophrenia; Undifferentiated schizophrenia; Catatonic schizophrenia; and Residual schizophrenia.

SUMMARY OF THE INVENTION

Some embodiments of the invention relate to compositions comprising beta-caryophyllene (BCP), methods of making the compositions and methods using BCP for the treatment of schizophrenia. Some embodiments of the invention relate to compositions comprising Cannabinoid Receptor Type 2 (CB2) receptor agonists, methods of making the compositions and methods using CB2 receptor agonists for the treatment of schizophrenia.

According to an aspect of some embodiments of the invention, there is provided a therapeutic composition comprising beta-caryophyllene (BCP) and a pharmaceutically effective carrier for use in treating schizophrenia. In some embodiments, the composition is for use in the treatment of a human subject. In some embodiments, the composition is for use in the treatment of a non-human subject.

In some embodiments, the schizophrenia is selected from the group consisting of paranoid schizophrenia; disorganized schizophrenia; undifferentiated schizophrenia; catatonic schizophrenia; and residual schizophrenia.

In some embodiments, the treating comprises treating at least one symptom of schizophrenia selected from the group consisting of a negative symptom of schizophrenia and a positive symptom of schizophrenia.

In some embodiments, the pharmaceutically effective carrier comprises dimethyl sulfoxide (DMSO). In some such embodiments, the pharmaceutically effective carrier comprises DMSO, saline and Cremophor EL. In some such embodiments, the pharmaceutically effective carrier comprises DMSO, saline and Cremophor EL at a ratio of 1:0.6:18 Cremophor EL:DMSO:saline.

In some embodiments, a single discrete unit (e.g., a single tablet, capsule, metered liquid) of the composition comprises BCP at a weight in the range of from about 25 to about 100 mg.

In some embodiments, the composition is formulated as an injectable solution dosage form. In some embodiments, the injectable solution is configured to be administered by a route selected from the group consisting of intravenous injection, intramuscular injection, intradermal injection, intraperitoneal injection, intrathecal injection and subcutaneous injection.

In some embodiments, the composition is formulated as an orally-administrable dosage form. In some such embodiments, the composition is formulated in a dosage form selected from the group consisting of a tablet, a capsule, a dragee, a powder, granules, and an ingestible solution, especially a tablet or capsule.

In some embodiments, the composition further comprises at least one additional antipsychotic agent. In some such embodiments, at least one additional antipsychotic agent is selected from the group consisting of chlorpromazine, haloperidol, perphenazine, fluphenazine, clozapine, risperidone, olanzapine, quetiapine, ziprasidone, aripiprazole, and paliperidone, or combinations thereof.

According to an aspect of some embodiments of the invention, there is also provided the use of beta-caryophyllene (BCP) and a pharmaceutically effective carrier in the manufacture of a composition (also known as a medicament) for treating schizophrenia in a subject in need thereof. In some embodiments, the composition is configured for use in the treatment of a human subject. In some embodiments, the composition is configured for use in the treatment of a non-human subject.

In some embodiments, the schizophrenia is selected from the group consisting of paranoid schizophrenia; disorganized schizophrenia; undifferentiated schizophrenia; catatonic schizophrenia; and residual schizophrenia.

In some embodiments, the treating comprises treating at least one symptom of schizophrenia selected from the group consisting of a negative symptom of schizophrenia and a positive symptom of schizophrenia.

In some embodiments, the pharmaceutically effective carrier comprises dimethyl sulfoxide (DMSO). In some such embodiments, the pharmaceutically effective carrier comprises DMSO, saline and Cremophor EL. In some such embodiments, the pharmaceutically effective carrier comprises DMSO, saline and Cremophor EL at a ratio of 1:0.6:18 Cremophor EL:DMSO:saline.

In some embodiments, a single discrete unit (e.g., a single tablet, capsule, metered liquid) of the composition that is manufactured comprises BCP at a weight in the range of from about 25 to about 100 mg.

In some embodiments, the composition is made as an injectable solution dosage form. In some embodiments, the injectable solution is configured to be administered by a route selected from the group consisting of intravenous injection, intramuscular injection, intradermal injection, intraperitoneal injection, intrathecal injection and subcutaneous injection.

In some embodiments, the composition is made as an orally-administrable dosage form. In some such embodiments, the dosage form selected from the group consisting of a tablet, a capsule, a dragee, a powder, granules, and an ingestible solution, especially a tablet or capsule.

In some embodiments, the composition further comprises at least one additional antipsychotic agent. In some such embodiments, at least one additional antipsychotic agent is selected from the group consisting of chlorpromazine, haloperidol, perphenazine, fluphenazine, clozapine, risperidone, olanzapine, quetiapine, ziprasidone, aripiprazole, and paliperidone, or combinations thereof.

According to an aspect of some embodiments of the present invention, there is also provided a method for treating schizophrenia in a subject in need thereof, the method comprising administering a therapeutic composition comprising beta-caryophyllene (BCP) and a pharmaceutically effective carrier. In some embodiments, the subject is a human subject. In some embodiments, the subject is a non-human subject.

In some embodiments, the schizophrenia is selected from the group consisting of paranoid schizophrenia; disorganized schizophrenia; undifferentiated schizophrenia; catatonic schizophrenia; and residual schizophrenia.

In some embodiments, the treating comprises treating at least one symptom of schizophrenia selected from the group consisting of a negative symptom of schizophrenia and a positive symptom of schizophrenia.

In some embodiments, the average daily amount of the BCP administered to the subject is from about 0.4 mg/kg to about 2 mg/kg.

In some embodiments, the pharmaceutically effective carrier comprises dimethyl sulfoxide (DMSO). In some such embodiments, the pharmaceutically effective carrier comprises DMSO, saline and Cremophor EL. In some such embodiments, the pharmaceutically effective carrier comprises DMSO, saline and Cremophor EL at a ratio of 1:0.6:18 Cremophor EL:DMSO:saline.

In some embodiments, the administering comprises injecting the composition to the subject. In some embodiments, the injecting comprises injecting by a route selected from the group consisting of intravenous injection, intramuscular injection, intradermal injection, intraperitoneal injection, intrathecal injection and subcutaneous injection.

In some embodiments, the administering comprises orally administering the composition to the subject.

In some embodiments, the method further comprises co-administering at least one additional antipsychotic agent. In some such embodiments, the at least one additional antipsychotic agent is selected from the group consisting of chlorpromazine, haloperidol, perphenazine, fluphenazine, clozapine, risperidone, olanzapine, quetiapine, ziprasidone, aripiprazole, and paliperidone, or combinations thereof.

In some such embodiments, the at least one additional antipsychotic agent is co-administered in a single dosage form together with the BCP. In some such embodiments, the at least one additional antipsychotic agent is co-administered in a dosage form separate from the BCP. In some such embodiments, the co-administration comprises sequential or simultaneous administration. In some such embodiments, the sequential administration comprises administration of the at least one additional antipsychotic agent prior to administration of the BCP. In some such embodiments, the sequential administration comprises administration of the at least one additional antipsychotic agent subsequent to administration of the BCP.

When found in nature, BCP (beta-caryophyllene) typically appears as a mixture of two pharmaceutically-active isomers E-BCP and Z-BCP, together with substantially inactive sesquiterpenes such as alpha-humulene and derivatives such as BCP oxide. Typically, natural sources include a greater proportion of E-BCP than Z-BCP.

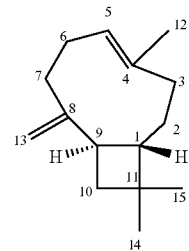

(E)-BCP

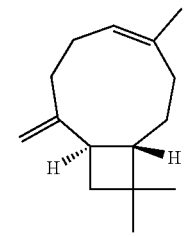

(Z)-BCP

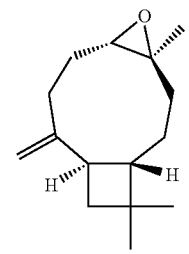

BCP oxide

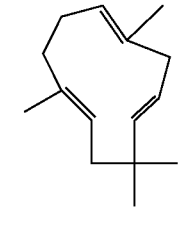

α-humulene

For implementing the teachings herein, the BCP includes both E-BCP and Z-BCP, alone or in combination.

In some embodiments, the BCP used for implementing the teachings herein is at least 65%, at least 75%, at least 85% and even at least 95% by weight E-BCP. In some embodiments, the BCP is substantially pure (at least 99% by weight) E-BCP.

In some embodiments, the BCP used for implementing the teachings herein is at least 65%, at least 75%, at least 85% and even at least 95% by weight Z-BCP. In some embodiments, the BCP is substantially pure (at least 99% by weight) Z-BCP.

In some embodiments, the BCP used for implementing the teachings herein is at least 65%, at least 75%, at least 85% and even at least 95% by weight E-BCP and/or Z-BCP.

In some embodiments, the BCP is substantially pure (at least 99% by weight) E-BCP and/or Z-BCP.

For example, in some embodiments the BCP used for implementing the teachings herein comprises 45-49% E-BCP, 45-49% Z-BCP, 1-5% BCP oxide and 1-5% alpha humulene.

For example, in some embodiments BCP used for implementing the teachings herein comprises 45-90% E-BCP, 5-30% Z-BCP, 1-5% BCP oxide and traces alpha humulene.

According to an aspect of some embodiments of the invention, there is also provided a composition comprising a CB2 receptor agonist and a pharmaceutically effective carrier for use in treating schizophrenia.

According to an aspect of some embodiments of the invention, there is also provided a use of a composition comprising a CB2 receptor agonist and a pharmaceutically effective carrier in the manufacture of a composition for treating schizophrenia in a subject in need thereof.

According to an aspect of some embodiments of the invention, there is also provided a method for the treating schizophrenia in a subject in need thereof, the method comprising administering a therapeutic composition comprising a CB2 receptor agonist and a pharmaceutically effective carrier.

Any suitable CB2 receptor agonist may be used in implementing the composition, the use or the method of treating, in some embodiments BCP and/or HU308. In some embodiments, the various features, options and embodiments are as explicitly discussed with reference to BCP.

In some embodiments, the teachings herein are applied to the treatment of human subjects, for example, humans suffering from schizophrenia.

In some embodiments, the teachings herein are applied to the treatment of non-human animal subjects suffering from schizophrenia.

Unless otherwise defined, all technical and scientific terms used herein have the same meaning as commonly understood by one of ordinary skill in the art to which the invention pertains. In case of conflict, the specification, including definitions, takes precedence.

As used herein, the terms "comprising", "including", "having" and grammatical variants thereof are to be taken as specifying the stated features, integers, steps or components but do not preclude the addition of one or more additional features, integers, steps, components or groups thereof.

As used herein, the indefinite articles "a" and "an" mean "at least one" or "one or more" unless the context clearly dictates otherwise.

As used herein, when a numerical value is preceded by the term "about", the term "about" is intended to indicate +/−10%.

As used herein, the term "treating" includes curing a condition, treating a condition, preventing a condition, treating symptoms of a condition, curing symptoms of a condition, ameliorating symptoms of a condition, treating effects of a condition, ameliorating effects of a condition, and preventing results of a condition As used herein a "therapeutic composition" refers to a preparation of one or more of the active ingredients with other components such as pharmaceutically-acceptable carriers and excipients. The purpose of a therapeutic composition is to facilitate administration of an active ingredient to a subject.

The term "pharmaceutically acceptable carrier" refers to a carrier or a diluent that does not cause significant irritation to a subject and does not substantially abrogate the activity and properties of the administered active ingredients. An adjuvant is included under these phrases. The term "excipient" refers to an inert substance added to a therapeutic composition to further facilitate administration of an active ingredient.

Therapeutic compositions used in implementing the teachings herein may be formulated using techniques with which one of average skill in the art is familiar in a conventional manner using one or more pharmaceutically-acceptable carriers comprising excipients and adjuvants, which facilitate processing of the active ingredients into a pharmaceutical composition and generally includes mixing an amount of the active ingredients with the other components. Suitable techniques are described in "Remington's Pharmaceutical Sciences," Mack Publishing Co., Easton, Pa., latest edition, which is incorporated herein by reference. For example, pharmaceutical compositions useful in implementing the teachings herein may be manufactured by one or more processes that are well known in the art, e.g., mixing, blending, homogenizing, dissolving, granulating, emulsifying, encapsulating, entrapping and lyophilizing processes.

Pharmaceutical compositions suitable for implementing the teachings herein include compositions comprising active ingredients in an amount effective to achieve the intended purpose (a therapeutically effective amount). Determination of a therapeutically effective amount is well within the capability of those skilled in the art, for example, is initially estimated from animal models such as monkey or pigs.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures:

FIG. 1A is a line graph showing changes in body weight at postnatal days 3 to 17 in mice treated with phencyclidine (PCP), PCP+BCP or control (vehicle) and FIG. 1B is a bar graph showing body weight for the 3 groups at postnatal day 17;

FIGS. 2A-2C relate to open field test at PND 16-17: FIGS. 2A and 2B are line graphs showing ambulation (2A) and rearing (2B) at PND 16-17 and FIG. 2C is a bar graph showing body weight at PND 17;

FIGS. 3A-3F relate to open field test at PND 16-17: FIGS. 3A and 3D are bar graphs showing body weight for males (3A) and females (3D), FIGS. 3B and 3E are line graphs showing ambulation in males (3E) and females (3F) and FIGS. 3C and 3F are line graphs showing rearing in males (3C) and females (3F);

FIGS. 4A and 4D are bar graphs showing body weight for males (4A) and females (4D), FIGS. 4B and 4E are line graphs showing rearing in males (4B) and females (4E) and FIGS. 4C and 4F are line graphs showing ambulation in males (4C) and females (4F);

FIGS. 5A and 5C are bar graphs showing response to startle for 8 week old males (5A) and females (5C); FIGS. 5B and 5D are line graphs showing percentage inhibition of pre-pulse inhibition for males (5B) and females (5D);

FIGS. 6A-6H relate to elevated plus maze test at age 13 weeks: female duration closed (6A), male duration closed (6B), female duration open (6C), male duration open (6D), female duration distal open (6E), male duration distal open (6F), female open/close duration (6G) and male open/close duration (6H);

FIGS. 7A-7I are bar graphs showing mRNA expression of cannabinoid receptors in 9 day old mice for glyceraldehyde 3-phosphate dehydrogenase (GAPDH) in the left cortex (7A), right cortex (7B) and brain stem (7G); for Cannabinoid Receptor Type 1 (CB1) in the left cortex (7C), right cortex (7D) and brain stem (7H); and for CB2 in the left cortex (7E), right cortex (7F), and brain stem (7I) for control mice and mice treated with PCP;

FIG. 8 is a Table detailing the percentage change (%) relative to control animals of protein expression of cannabinoid receptors in 2 week old mice;

FIGS. 9A-9C are bar graphs showing protein expression of 67 kDa glutamic acid decarboxylase (GAD67)/actin in the left cortex (9A), right cortex (9B) and brain stem (9C) of 2-week old mice treated with saline or PCP;

FIGS. 11A and 11B are schematic representations of the endocannabinoid synthesizing and degrading pathways as described in Anavi-Goffer, ChemBioChem 2009;

FIGS. 12A-12C relate to PND17 using a DMSO-based vehicle: line-graph showing male ambulation (12A), line-graph showing male rearing (12B) and line graph showing male body weight (12C);

FIGS. 13A-13C relate to PND16: line-graph showing body weight over PND 3-17 (13A), line-graph showing male and female ambulation (13B) and line-graph showing male and female rearing (13C);

FIGS. 14A-14E show results demonstrating that BCP treatment at adolesence reversed the effect of PCP on ambulation but did not affect body weight: line graph of body weight at PND 40-68 (14A), bar graph of female and male body weight at PND63 (14B), line graph of male ambulation at PND 63 (14D), line graph of female ambulation at PND 63 and line graph of male and female ambulation at PND 63;

FIGS. 15A-15C show results demonstrating that BCP treatment at adolesence reversed the effect of PCP on rearing: line graph of male and female rearing at PND63 (15A), line graph of male rearing at PND63 (15B) and line graph of female rearing at PND63 (15C);

FIGS. 16A-16C show results demonstrating that BCP treatment at adolesence reversed the effect of PCP on PPI: line graph of % PPI at PND68 (16A); bar graph of female startle response at PND68 (16B) and bar graph of male startle response at PND68 (16C);

FIGS. 17A-17C show results demonstrating that BCP treatment at adolesence reversed the effect of PCP on the response to tone (PPI test): line graph of response to tone at PND68 (17A); line graph of female response to tone at PND68 (17B) and line graph of male response to tone at PND68 (17C);

FIGS. 19A-19F show results demonstrating that BCP treatment at adolesence did not reverse the effects of PCP in plus maze test: open/close duration at PND 64 (19A), open/(close+open) duration at PND 64 (19B), distal open/(close+open) duration at PND 64 (19C), open/close frequency at PND 64 (19D), open/(open+close) frequency at PND 64 (19E) and distal open/(open+close) frequency at PND 64 (19F);

FIGS. 20A-20E show results demonstrating that BCP treatment at adolesence reversed the effects of PCP on the time spent in the hidden zone (behavior in the Phenotyper cage): bar graph of female hidden zone duration at PND 91 (20A), bar graph of male hidden zone duration at PND 91 (20B), bar graph of male and female hidden zone duration at PND 91 (20C), bar graph of male hidden zone frequency at PND 91 (20D) and bar graph of female hidden zone frequency at PND 91 (20E);

FIGS. 22A-22F show results demonstrating that BCP treatment at adolesence on the time spent at drinking and food zones (Phenotyper cage): bar graph showing male food zone duration at PND91 (22A), bar graph showing female food zone duration at PND91 (22B), bar graph showing male and female food zone duration at PND91 (22C), bar graph showing male drink zone duration at PND91 (22D), bar graph showing female drink zone duration at PND91 (22E) and bar graph showing male and female drink zone duration at PND91 (22F);

FIGS. 25A-25I show results demonstrating that BCP treatment at adolesence reversed the effect of PCP on attention at PND106 (PPI test): bar graph of female startle at PND 106 (25A), bar graph of male startle at PND 106 (25B), bar graph of male and female startle at PND 106 (25C), line graph of female response to tone of varying intensity (25D), line graph of female response to tone of varying intensity (25E), line graph of female response to tone of varying intensity (25F), line graph of % prepulse inhibition for females at PND 106 (25G), line graph of % prepulse inhibition for males at PND 106 (25H) and line graph of % prepulse inhibition for males and females at PND 106 (25I);

DESCRIPTION OF SOME EMBODIMENTS OF THE INVENTION

Figure 1B:
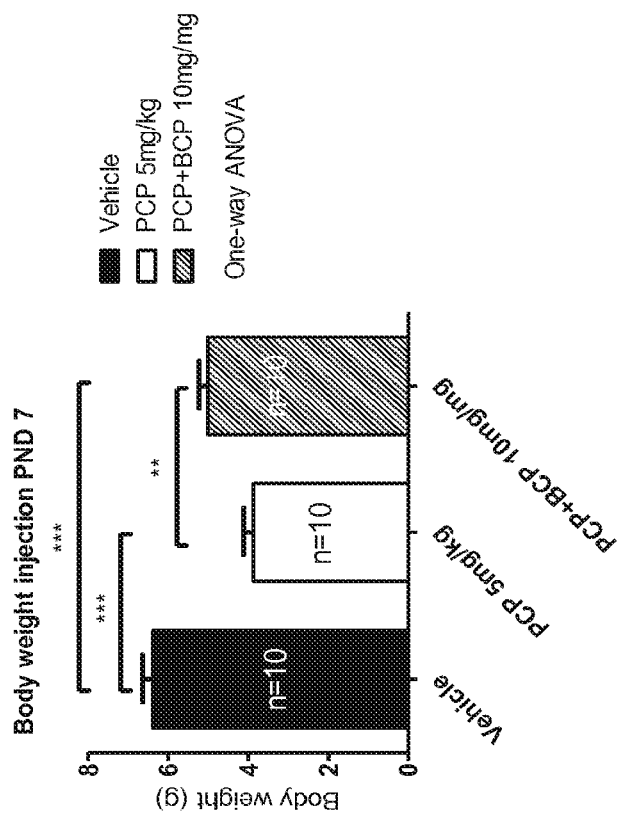
FIGS. 1A and 1B relate to mouse body weight at PND 16-17.

Some embodiments of the invention relate to compositions comprising beta-caryophyllene (BCP), methods of making the compositions and methods using BCP for the treatment of schizophrenia. Some embodiments of the invention relate to compositions comprising Cannabinoid Receptor Type 2 (CB2) receptor agonists, methods of making the compositions and methods using CB2 receptor agonists for the treatment of schizophrenia.

The principles, uses and implementations of the teachings herein may be better understood with reference to the accompanying description and figures. Upon perusal of the description and figures present herein, one skilled in the art is able to implement the invention without undue effort or experimentation.

The Cannabinoid Receptor Type 2 (CB2) is a guanine nucleotide-binding protein (G protein)-coupled receptor that in humans is encoded by the CNR2 gene.

Recent studies have identified the cannabinoid CB2 receptor in the brain. Up-regulation of CB2 receptor expression in the brain during central nervous system pathologies has been demonstrated for certain neurological diseases.

Beta-caryophyllene (BCP, CAS 87-44-5) is a CB2-receptor agonist (Gertsch et al. 2008, Anavi-Goffer et al., 2012). The fact that orally-administered BCP is absorbed by the digestive tract and becomes systemically available and apparent substantial non-toxicity makes BCP attractive as a potential active pharmaceutical ingredient.

The role of CB2 receptor agonists in general, and RCP in particular, in the treatment of schizophrenia, has not previously been studied.

The Inventors have studied the effect of BCP in a murine model of schizophrenia, produced by administration of the N-methyl-D-aspartic acid (NMDA) antagonist, phenylcyclidine (PCP). Administration of phencyclidine to rats (e.g. Josselyn and Vaccarino, 1998; Wang & Johnson, 2005; Ballmaier, 2007; Takahashi, 2006) or mice (e.g. Long, 2006; Hashimoto 2005) has been used as an animal model for schizophrenia. Phencyclidine may be administered acutely or chronically, during adulthood or during postnatal development, using different dose ranges (2.5 mg/kg to 20 mg/kg). In order to induce chronic, long lasting schizophrenic-like behaviors and neurochemical changes in the endocannabinoid system, the Inventors have now developed a neonatal mouse model, based on a neonatal phencyclidine model previously described for rats (Takahashi, 2006). As the Inventors have extensively studied the endocannabinoid system in Sabra strain mice (Harlan, Israel), see for example Fride 2005 and Fride 2007, these mice have been used in the present study.

The Inventors have found that following administration of PCP, the CB2 receptor expression level is selectively down-regulated in different brain areas. Furthermore, up-regulation of putative CB2 receptor expression has been detected in the right cortex and basal ganglia/diencephalon of mice which were neonatally treated with phencyclidine. These results support some aspects of the teachings herein, where putative CB2 receptors are up-regulated in specific brain areas in schizophrenia.

Thus, according to an aspect of some embodiments of the teachings herein, there is provided a composition comprising beta-caryophyllene (BCP) and a pharmaceutically effective carrier for use in treating schizophrenia.

According to an aspect of some embodiments of the teachings herein, there is also provided the use of beta-caryophyllene (BCP) and a pharmaceutically effective carrier in the manufacture of a medicament for treating schizophrenia in a subject in need thereof.

In some embodiments, such a composition is configured for administration to a human subject. In some embodiments, such a composition is configured for administration to a non-human animal subject.

According to an aspect of some embodiments disclosed herein, there is also provided a method for treating schizophrenia in a subject in need thereof, the method comprising administering a pharmaceutically-effective amount of beta-caryophyllene (BCP) to the subject. In some embodiments, the subject is a human subject. In some embodiments, the subject is a non-human animal.

The efficacy of the methods and compositions according to the teachings herein are demonstrated in the experimental section hereinbelow.

According to some embodiments, the compositions and methods of treatments disclosed herein are useful for treating one or more of paranoid schizophrenia; disorganized schizophrenia; undifferentiated schizophrenia; catatonic schizophrenia; and residual schizophrenia.

In some embodiments, the compositions and methods of treatments disclosed herein are useful in the treatment of a negative symptom of schizophrenia.

In some embodiments, the compositions and methods of treatments disclosed herein are useful in the treatment of a positive symptom of schizophrenia.

The duration of treatment according to the method of treating schizophrenia according to the teachings is any suitable duration as determined by a treating health-care professional, typically a psychiatric doctor.

In some embodiments of the method of treating schizophrenia according to the teachings herein, the average daily dose of BCP administered to a human subject is from about 0.4 mg/kg to about 2 mg/kg, such as, for example, from about 0.4 mg/kg to about 1.5 mg/kg, from about 0.4 mg/kg to about 1.8 mg/kg, from about 0.4 mg/kg to about 1.6 mg/kg, from about 0.4 mg/kg to about 1.4 mg/kg, from about 0.4 mg/kg to about 1.2 mg/kg, from about 0.4 mg/kg to about 1 mg/kg, from about 0.4 mg/kg to about 0.8 mg/kg, from about 0.4 mg/kg to about 0.6 mg/kg or from about 0.4 mg/kg to about 0.5 mg/kg.

In some embodiments of the method of treating schizophrenia according to the teachings herein, the average daily dose for a human subject (especially an adult human, weighing between about 40 kg and about 120 kg) is in the range of from about 25 mg to about 100 mg, such as about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg.

In some embodiments of the method of treating schizophrenia according to the teachings herein, the average daily dose is administered with a frequency of between about once a week to about 3 times per day, for example once per week, twice per week, 3 times per week, 4 times per week, 5 times per week, 6 times per week, once per day, twice per day or 3 times per day.

In some embodiments, a composition according to the teachings herein is provided as or made as a dosage form including a plurality of discrete units (e.g., discrete solids or metered liquids), especially discrete solid units such as pills (including tablets and caplets) and capsules (including gelcaps), where each unit includes BCP in the range of from about 25 mg to about 100 mg, such as about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg. In some such embodiments, such a dosage form is exceptionally useful for the once-daily administration of the desired average daily dosage.

According to some embodiments, the composition disclosed herein may be administered by any suitable route of administration, including but not limited to oral administration, parenteral administration (including intravenous injection, intramuscular injection, intradermal injection, intraperitoneal injection, intrathecal injection and subcutaneous injection), and rectal administration. That said, in some embodiments, oral administration is preferred due to the proven oral availability and substantial-non toxicity of BCP.

For oral administration, the composition disclosed herein may comprise a pill, a capsule, a dragee, a powder, granules, an ingestible solution (such as a liquid, a gel, a syrup, or a suspension) and the like, for oral ingestion by a subject. In a preferred embodiment, a composition for oral administration comprises a pill or a capsule.

In a preferred embodiment, the composition is a gastroresistant orally-administrable dosage form, that is to say, an orally-administrable dosage form configured to carry the BCP through the stomach to be released into contact with the digestive tract only after passage through the duodenum. For example, in some such embodiments, the composition is in the form of a gastroresitant soft gel capsule, comprising between 25 mg and about 100 mg BCP in a carrier comprising vegetable oil. Some embodiments of the method, when implemented with an adult human subject, comprise orally ingesting a single such capsule twice a day for at least one month, so that the average daily dose is between about 50 mg and about 200 mg BCP.

In some embodiments, the composition described herein further comprises at least one additional antipsychotic agent, such as, for example, a typical antipsychotic agent (including, but not limited to, one or more of chlorpromazine, haloperidol, perphenazine, or fluphenazine), and/or an atypical antipsychotic agent (including, but not limited to, one or more of clozapine, risperidone, olanzapine, quetiapine, ziprasidone, aripiprazole, and paliperidone), or combinations thereof.

In some embodiments of the method of treatment, the BCP is administered together with at least one additional antipsychotic agent, such as, for example, a typical antipsychotic agent (including, but not limited to, one or more of chlorpromazine, haloperidol, perphenazine, or fluphenazine), and/or an atypical antipsychotic agent (including, but not limited to, one or more of clozapine, risperidone, olanzapine, quetiapine, ziprasidone, aripiprazole, and paliperidone), or combinations thereof.

In some embodiments where the BCP and an antipsychotic agent are administered together, BCP and the additional antipsychotic agent are co-administered in a single dosage form.

In some embodiments where the BCP and an antipsychotic agent are administered together, BCP and the additional antipsychotic agent are co-administered in separate dosage forms, either sequentially or simultaneously. For example, the additional antipsychotic agent may be administered prior to administration of BCP, or the additional antipsychotic agent may be administered subsequent to administration of BCP.

Although not wishing to be bound to any one theory, the Inventors consider that it is likely that at least part, if not all, of the herein demonstrated efficacy of BCP in treating schizophrenia relates to the CB2 receptor agonist properties of BCP.

Thus, according to an aspect of some embodiments of the teachings herein, there is provided a composition comprising a CB2 receptor agonist and a pharmaceutically effective carrier for use in treating schizophrenia.

According to an aspect of some embodiments of the teachings herein, there is also provided the use of a CB2 receptor agonist and a pharmaceutically effective carrier in the manufacture of a medicament for treating schizophrenia in a subject in need thereof.

According to an aspect of some embodiments of the teachings herein, there is also provided a method for treating schizophrenia in a subject in need thereof, the method comprising administering a pharmaceutically-effective amount of a CB2 receptor agonist to the subject.

Exemplary embodiments of the teachings herein are discussed hereinbelow with reference to specific materials, methods and examples. The material, methods and examples discussed herein are illustrative and not intended to be limiting. In some embodiments, methods and materials similar or equivalent to those described herein are used in the practice or testing of embodiments of the invention. It is to be understood that the invention is not necessarily limited in its application to the details of construction and the arrangement of the components and/or methods set forth in the following description and/or illustrated in the drawings. The invention is capable of other embodiments or of being practiced or carried out in various ways.

EXAMPLES

Materials and Methods

BCP was obtained from Sigma-Aldrich (St. Louis, Mo., USA), catalogue Nr. W225207 and further purified using preparative HPLC (HP1090 series; column, PEGASIL ODS (Senshu Sci. i.d. 10×250 mm); solvent, 70% $CH_3OH$; flow rate, 2.0 mL/min; detection, UV 220 nm] to remove other sesquiterpenes. GC-MS analysis showed that the BCP used in the below included 95% E-BCP, 3% Z-BCP, 1% BCP Oxide and traces of alpha humulene. AM630 was obtained from Cayman Chemical Company (Ann Arbor, Mich., USA). PCP, Cremophor EL and DMSO were obtained from Sigma-Aldrich (St. Louis, Mo., USA).

Animal Model of Schizophrenia:

The mouse model of schizophrenia was established. Phencyclidine (PCP), an NMDA antagonist which induces schizophrenia and psychotic effects in humans, was administered to murine pups (injection of 5 mg/kg in saline) on postnatal days 3, 5, 7, 9, 11, 13, and 16. This treatment induces long-lasting schizophrenic-like effects in mice that lasted into adulthood. The therapeutic effects of beta-caryophyllene, a dietary cannabinoid and CB2 receptor agonist, in accordance with the teachings herein were evaluated.

I. Treatment of Mice with Bcp at Postnatal Days 3-16

BCP (final dose 10 mg/kg in 1:0.6:18 Cremophor EL:ethanol:saline) was administered by injection 1 hour after PCP. Results were obtained from two different litters, each of which was divided into 3 groups:

Group 1: vehicle (n=6 and 4 pups, respectively);
Group 2: PCP (n=6 and 5 pups, respectively);
Group 3: PCP+BCP (n=5 and 5 pups, respectively).

In FIG. 17 BCP (final dose 10 mg/kg in 1:0.6:18 Cremophor EL:DMSO:saline) was administered by injection 1 hour after PCP. Results were obtained from one litter which was divided into the three groups.

Assessment of Positive/Negative Schizophrenic-Like Behavior:

Open-Field Test (Crossing and Rearing)

Mice were assessed for hyperactivity behavior on postnatal day 16 (FIG. 2). Mice were placed in the center of a transparent glass cube cage 30×40 λ31 cm divided into squares of 7.5×7.5 cm. The number of squares and rearing activity were counted for 8 min.

Positive Symptoms. Prepulse Inhibition (PPI) of the Startle Reflex

In this experimental model, a weak stimulus (74-90 dB tone) inhibited the subsequent response to a strong stimulus (120 dB tone). Reduced prepulse inhibition of the startle reflex (PPI) was taken as an index of the positive symptoms of schizophrenia (Josselyn and Vaccarino, 1998).

PPI was assessed similarly to the method described by Varty et al. In the employed model, mice were placed in a startle chamber and allowed to acclimate for 5 min. A loudspeaker produced a 65 dB background white noise or the various acoustic pre-pulse stimuli (dB): 74, 78, 82, 86, and 90 (20 ms). A 120 dB (40 ms) stimulus was given first to induce a response to startle. The response of the mouse was transduced and stored by a computer. Each test session lasted for 11 min and consisted of 5 presentations of each of the trial types presented in random order and separated by 15 second intervals. The amount of prepulse inhibition was calculated as % PPI=[1−(startle response for prepulse+pulse)/(startle response for pulse alone)]×100.

Negative Symptoms

Anxiety as measured by the paucity of time spent on the two, anxiety-provoking, open arms (as opposed to the two enclosed arms) of an "Elevated Plus Maze" was used as a parameter of negative symptoms of schizophrenia (Josselyn and Vaccarino, 1998). The plus maze was elevated 50 cm above the table top. Behavior of each mouse was recorded for 5 min by a video camera and scored using the "EthoVision" software (Noldus Information Technology, Wageningen, The Netherlands), measuring the number of entries as well as the amount of time spent in each arm, open or closed. Increased time spent in the closed arms indicated increased anxiety. Increased time spent in the opened arms indicated anxiolytic behavior (reduced stress).

Results

Body Weight

Figure 1A:
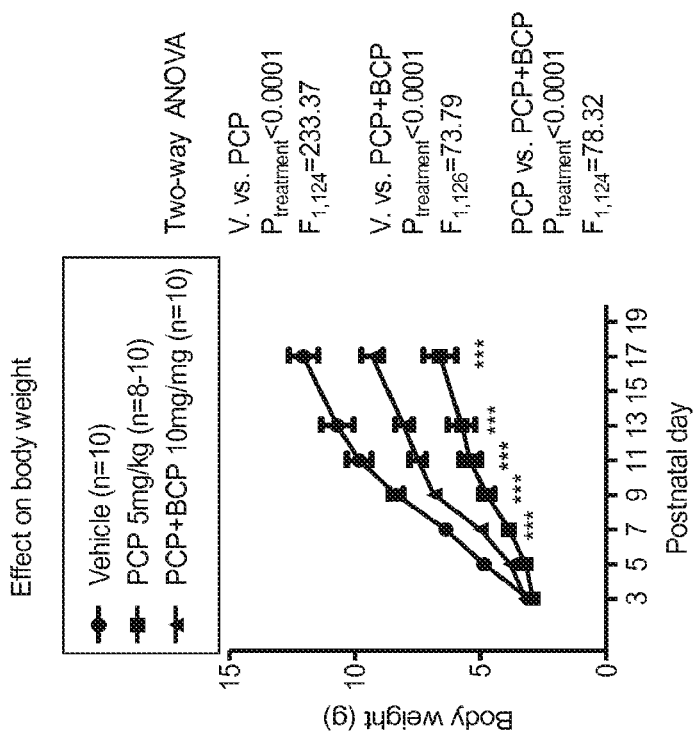

Body weight was recorded at each day of injection (FIG. 1A). PCP was shown to significantly reduce the body weight. The results show that BCP significantly reversed the inhibitory effect of PCP on body weight ($p<0.0001$ for PCP+BCP vs. PCP).

It was shown that at PND 7, PCP induced a significant reduction in body weight. BCP reversed the reduction in body weight during the first week of life (FIG. 1B) but, under these conditions (injections in ethanol-based vehicle as described above) did not restore the weight completely. However, when vehicle mixture was changed to DMSO-based, BCP completely reversed the effect of PCP on body weight (FIG. 12C).

At postnatal day (PND) 17, the difference between vehicle- and PCP-treated groups in body weight was still significant ($p<0.0001$) (FIG. 2C). There was no significant difference between groups treated with PCP with or without BCP.

Rearing and Exploration

At PND 17, at the end of treatment with BCP, locomotor activity, hyperactivity, and exploratory behaviors were tested with the open-field test (FIGS. 2A, 2B). PCP significantly inhibited both ambulation and rearing behaviors. Treatment with BCP reversed the effects of PCP on rearing and exploration. In addition, it is seen that the effect of BCP is not dependent on ethanol as its solvent. It is seen that a DMSO-based carrier completely reversed the effects of PCP on ambulation (FIG. 12A) and rearing behavior (FIG. 12B).

Results According to Sex

Changes in body weight and results from the open-field test at PND 17 were separated according to the sex of mice (FIGS. 3A-F).

Figure 3B:
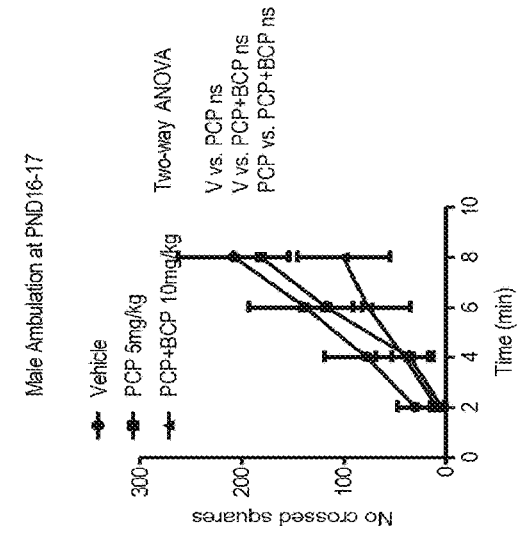
Figure 3C:
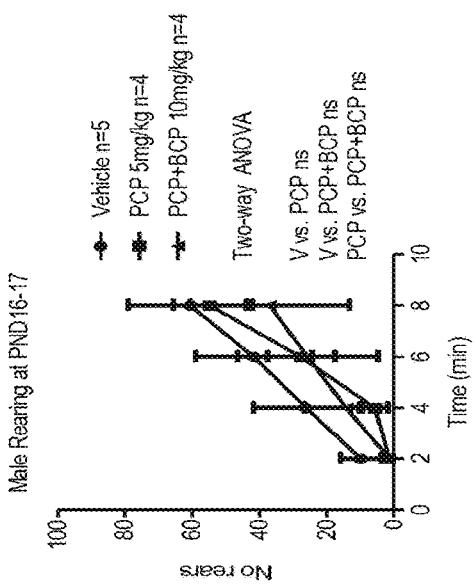
Figure 3A:
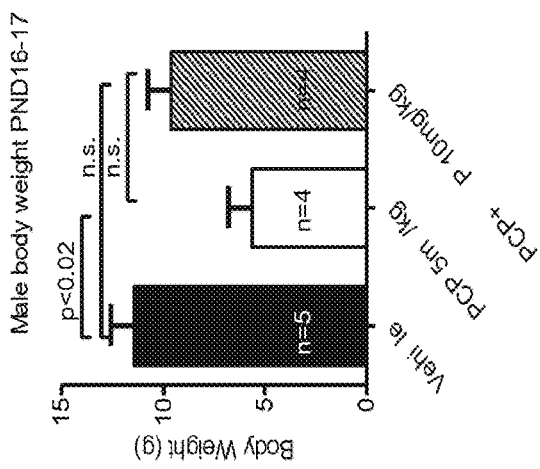

Females appeared to be more sensitive to the effect of PCP (ambulation $p<0.006$; $p<0.03$ rearing). Treatment with BCP reversed a proportion of the effects of PCP on ambulation and rearing behavior of female mice (FIGS. 3E, 3F, respectively) but not the effect of PCP on body weight (FIG. 3D). Locomotor activity of male mice appeared to be less sensitive to the treatment of PCP or PCP+BCP (FIGS. 3A-3C). However, the effect of BCP on PCP-induced reduction of body weight in male mice appeared to be more prominent (FIG. 3A).

These results suggest that in some embodiments the administration of BCP for the treatment of schizophrenia has a different effect on male and female mice, being more effective in the treatment of female mice.

Mice were re-evaluated in the open-field test at PND 35-37. Results of body weight, rearing and ambulation were separated according to the sex of mice (FIGS. 4A-F). Treatment with BCP significantly reversed the effect of PCP on female body weight (FIG. 4D). At this age there was no significant difference in male body weight between the groups (FIG. 4A).

Figure 4B:
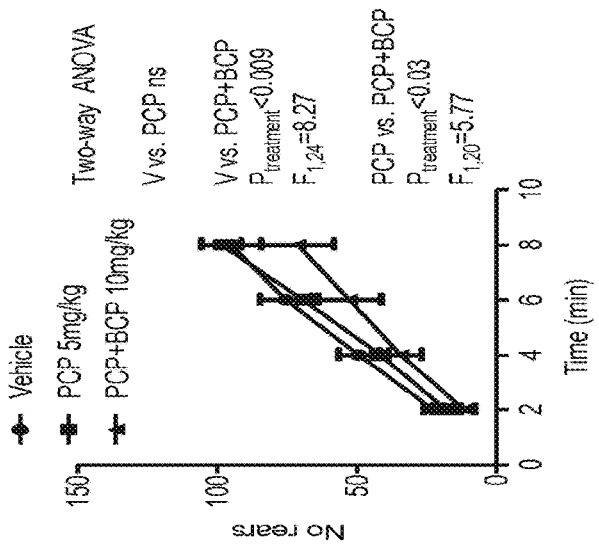
FIGS. 4A-4F relate to open field test at PND 35-37.

In males, treatment with BCP significantly reduced rearing behavior as compared to vehicle and PCP-treated groups (FIG. 4B).

Figure 4C:
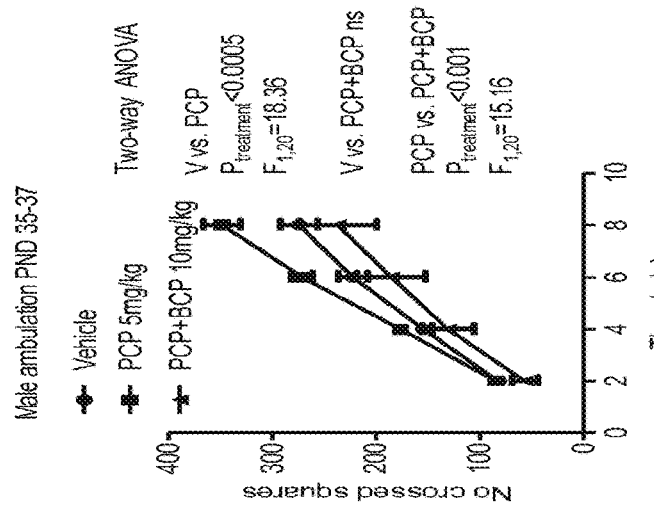
Figure 4A:
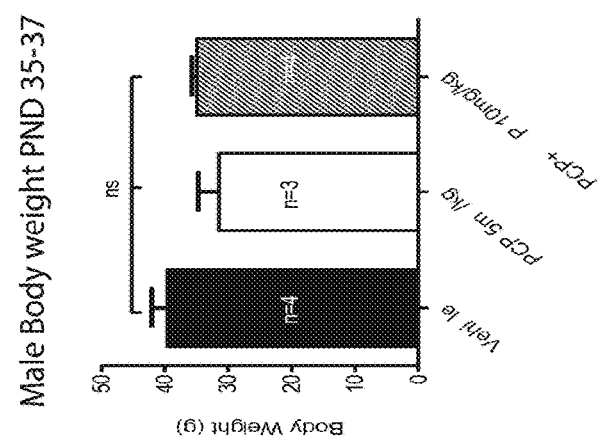
Figure 4E:
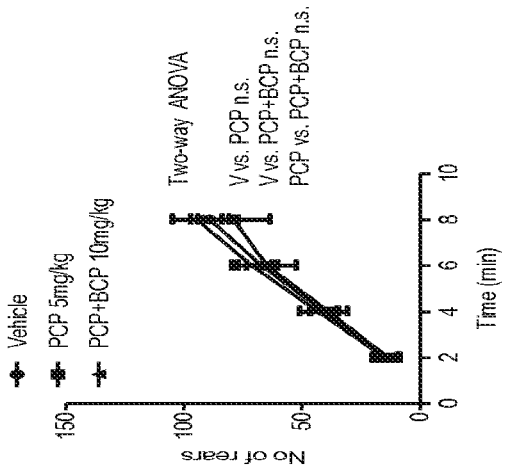
Figure 4F:
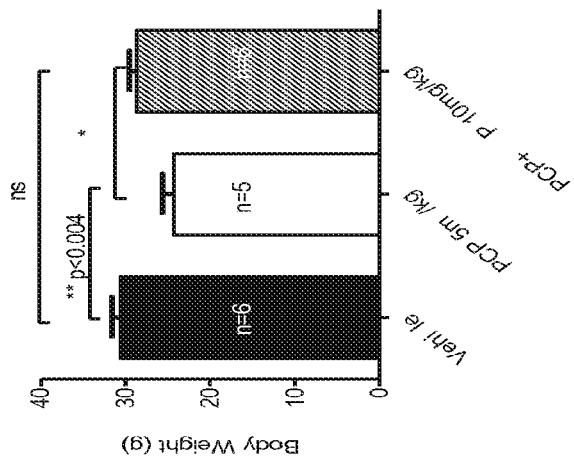
Figure 4D:
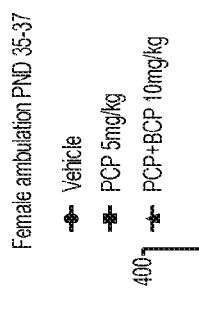

In males, treatment with PCP significantly increased the locomotor activity compared with vehicle treatment, while administration of BCP reduced locomotor activity (FIG. 4C). In females, no differences in rearing and exploration behaviors were seen between the different groups (FIGS. 4E, 4F, respectively).

It was concluded that treatment with BCP significantly reversed the effect of PCP in males.

Prepulse Inhibition Testing

Mice were tested at age 8 weeks in the Pre-Pulse Inhibition test (FIGS. 5A-D).

Response to Startle

Figure 5B:
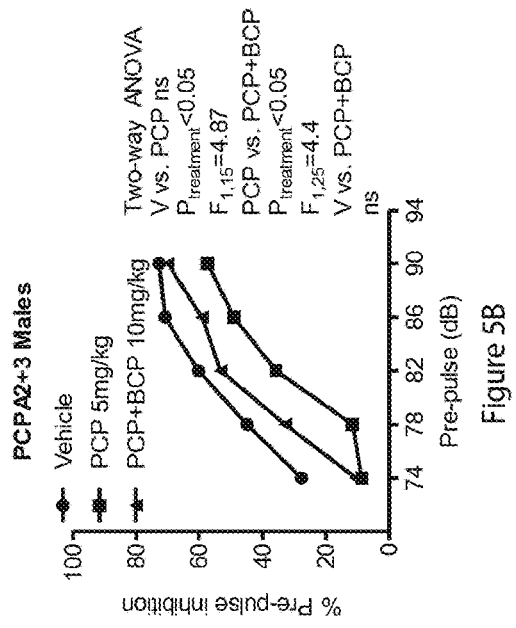
FIGS. 5A-5D relate to pre-pulse inhibition at age 8 weeks.
Figure 5D:
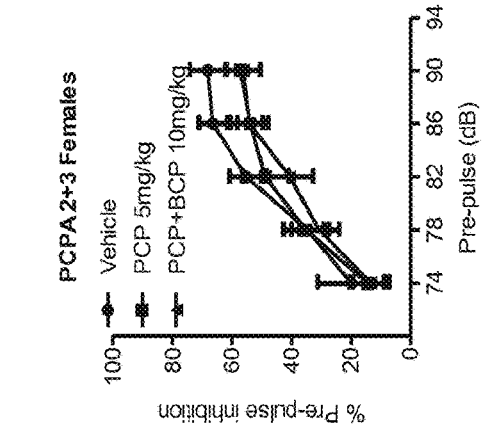
Figure 5A:
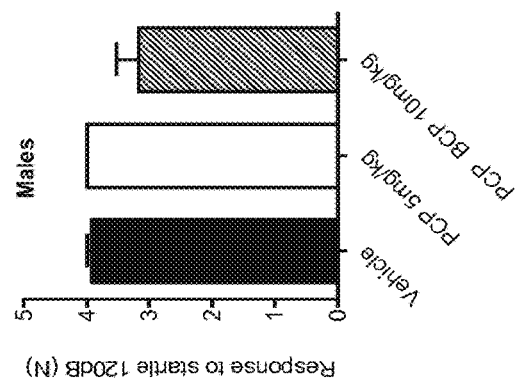
Figure 5C:
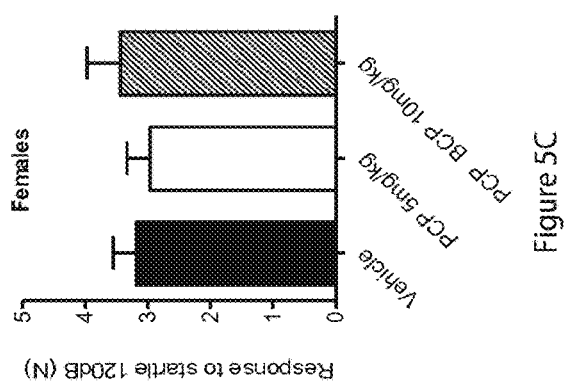
Figure 6A:
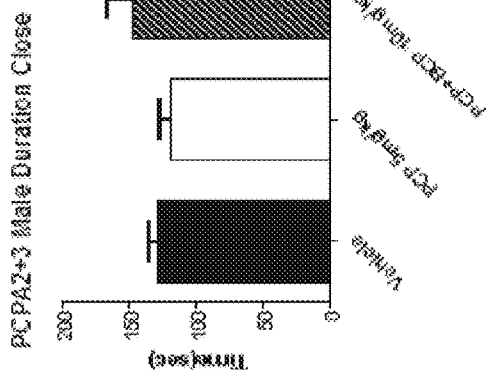
Figure 6B:
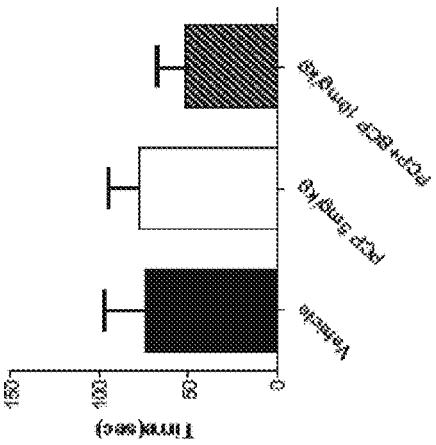
Figure 6C:
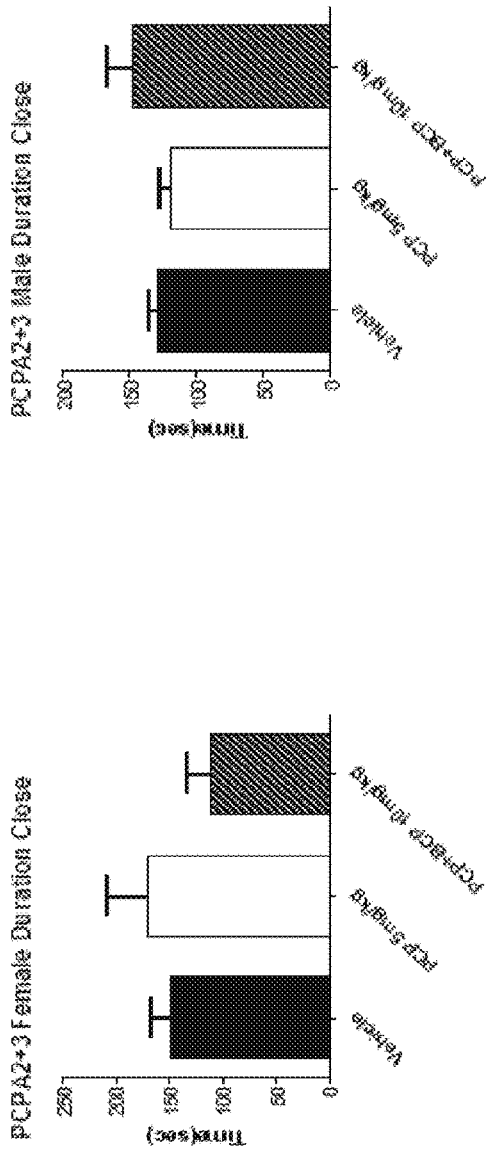
Figure 6D:
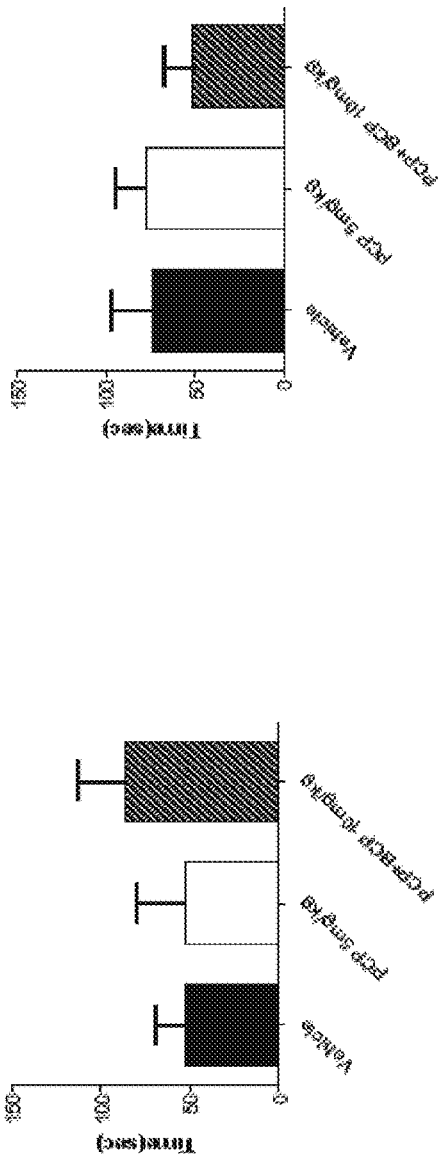

The response to startle stimuli was not significantly different between groups (in males (FIG. 5A) or in females (FIG. 5C). It was concluded that mice in all groups had no problem in hearing and were not apathetic.

% Inhibition

Males treated with PCP showed a significant reduction in their ability to adjust to sound stimulus as compared to vehicle treated mice. BCP reversed this effect (FIG. 5B).

No significant difference in in the ability to adjust to sound stimulus was seen in females for the PCP-treated group or PCP+BCP treated group (FIG. 5D).

It was concluded that treatment with BCP significantly reversed the effect of PCP on the sensorimotor-gate in males.

Elevated-Plus Maze Test

At age 13 weeks old, mice were tested in the Elevated-Plus Maze test which indicates the level of anxiety (FIGS. 6A-H).

Phencyclidine alters the level of anxiety. However its effect is dependent on the strain of mice, sex and possibly age (Turgeon, 2011; Wily, 1995).

There was no significant change in the time spent in the closed arm or open arm (all length of arm), for either females or males (FIGS. 6A, 6B, 6C, 6D, respectively).

PCP reduced the time spent in the distal end of the opened arm (the very far end of the arm from the center) for females, and BCP reversed this effect (FIGS. 6E, 6G). In FIGS. 6F, 6H, PCP increased the time spent in the distal end of the opened arm (the very far end of the arm from the center) for males, and BCP reversed this effect.

It was concluded that PCP induced anxiety in female mice and anxiolytic effect in male mice. BCP reversed both effects.

Expression Level of CB1 and CB2 Receptor in Mice at 9 Days Old (mRNA) or 2 Weeks Old (Protein)

Brain tissue of control mice (saline treated) and mice treated with PCP were analyzed in the left and right cortex and brain stem (FIGS. 7A-I; FIG. 8. Results from the cortex and brain stem were reported by the Inventors in 2011 (Anavi-Goffer et al).

No difference in GAPDH was seen in the left cortex, right cortex or brain stem (FIGS. 7A-7C, respectively).

No significant increase in mRNA expression of CB1 receptor was found in the left or right cortex of the PCP-treated mice (FIGS. 7D, 7E, respectively). A significant increase in mRNA expression of CB1 receptor was found in the brain stem of the PCP-treated mice (FIG. 7F).

A significant increase in mRNA expression of CB2 receptor was found in the left cortex of the PCP-treated mice (FIG. 7G) but in the right cortex there was no difference between control and PCP-treated mice (FIG. 7H). A significant increase in mRNA expression of CB2 receptor was found in the brain stem of the PCP-treated mice (FIG. 7I).

It is noteworthy that these results are the opposite of the observed in Western blotting, (FIG. 8) being about 50 kDa (the predicted molecular weight of the CB2 receptor) but in line with these at 64 kDa, suggesting that the CB2 receptor may form a complex with another protein X. This suggests that the change in cannabinoid receptor expression is specific (as no change was found for GAPDH or actin). This also suggests a malfunction in the regulation of cannabinoid receptor synthesis, leading to the accumulation of cannabinoid receptor mRNA in the left cortex and brain stem. On the other hand, synthesis in the right cortex appeared to lead to the formation of CB2 receptor-protein X complexes.

Expression Level of GAD67 in Mice at 9 Days Old (mRNA) or 2 Weeks Old (Protein)

Figures 9D, 9E, 9F:
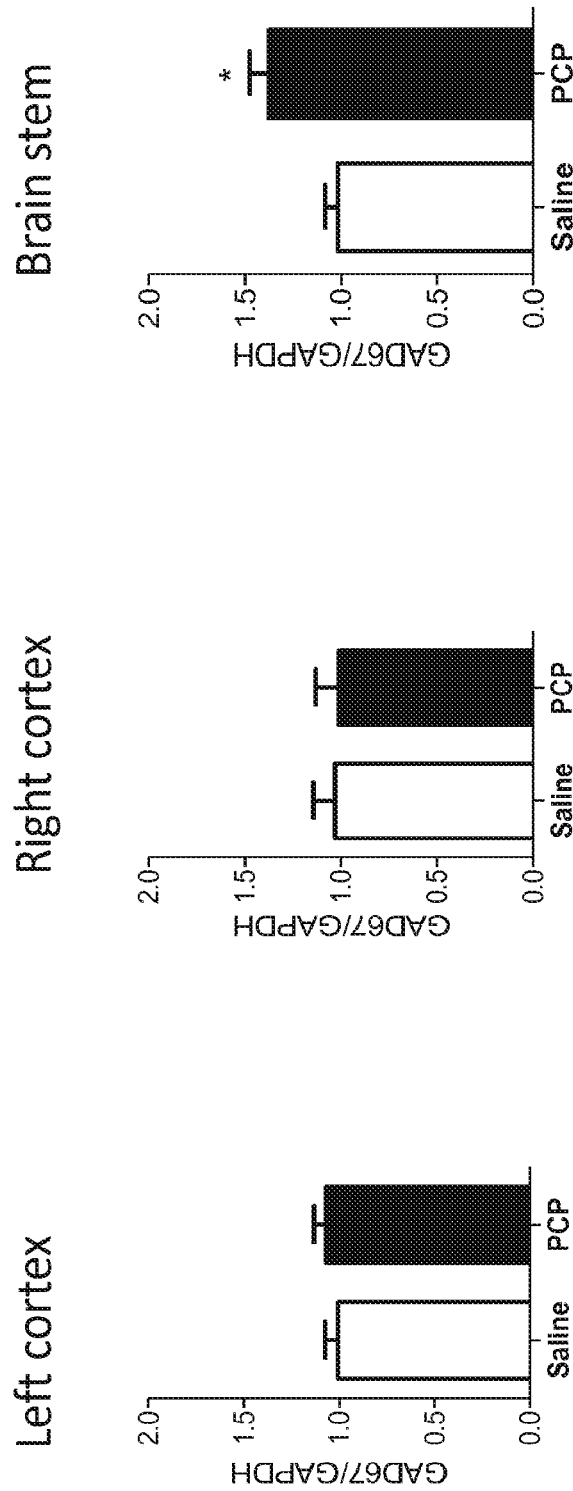
FIGS. 9D-9F are bar graphs showing protein expression of 67 kDa glutamic acid decarboxylase (GAD67)/actin in the left cortex (9D), right cortex (9E) and brain stem (9F) of 9-day old mice treated with saline or PCP.

Brain tissue of control mice and mice treated with PCP were analyzed for GAD67, a neurochemical marker for schizophrenia (FIG. 9A-F). In the left cortex, GAD67 protein level was significantly decreased (FIG. 9A) but no change was found at the mRNA level FIG. 9D). In the right cortex, the reduction in protein level of GAD67 did not reach a significant level and no change was seen in the mRNA level (FIG. 9B, FIG. 9E). In the brain stem, GAD67 mRNA level was increased in the PCP-treated group (FIG. 9F), although the results of Western blotting showed a non-significant reduction in GAD67 protein level (FIG. 9C). This suggests that there might be a common mechanism which links the changes in GAD67 to those of CB1 and CB2, and this mechanism may be related to the function of GABAergic neurons.

Expression of MGL in 2 Week Old Mice

Figure 10B:
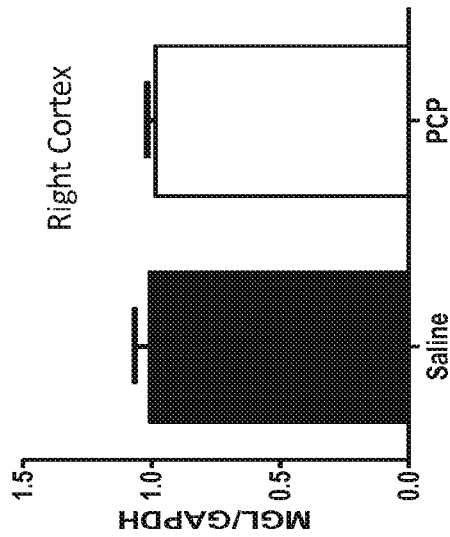
FIGS. 10A-10C relate to monoacylglycerol lipase (MGL) expression in 2 week old mice treated with saline or PCP: bar graph relating to the left cortex (10A), bar graph relating to the right cortex (10B) and Western blot (10C)
Figure 10A:
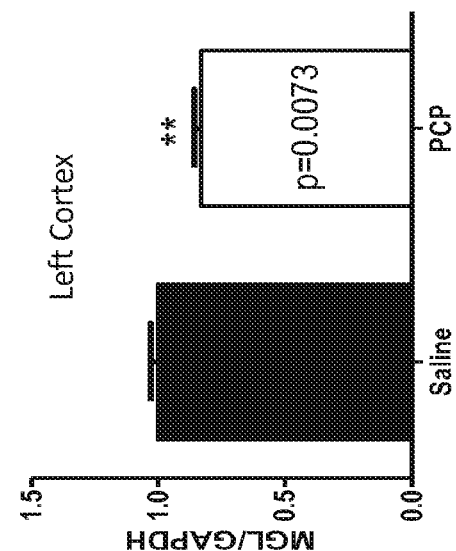
Figure 10C:
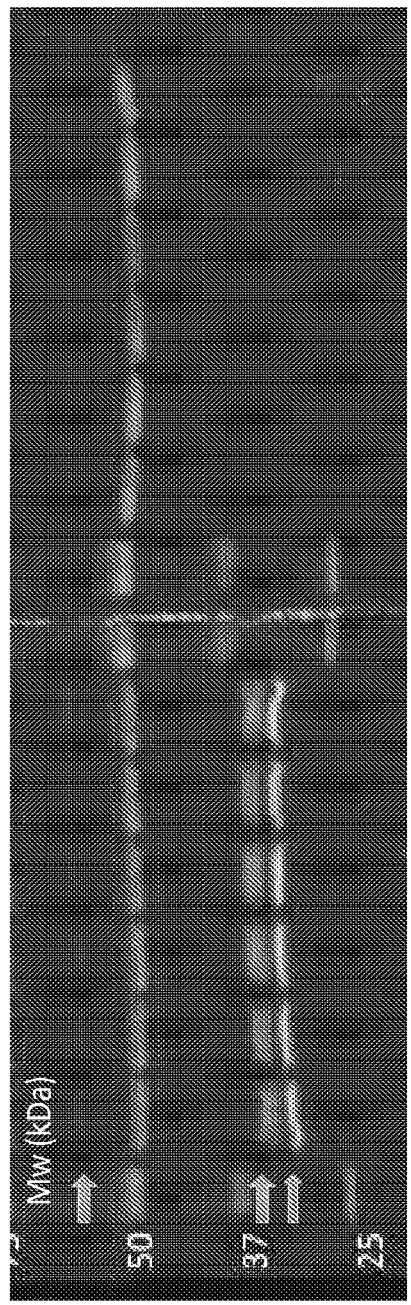

Brain tissues were analyzed for MGL, an enzyme which degrades 2-AG an endocannabinoid (FIGS. 10A-C, FIG. 11B) in control mice and mice treated with PCP. mRNA levels of MGL decreased in the left cortex of the PCP-treated group (FIG. 10A), but not in the right cortex (FIG. 10B). The direction of these results was correlated with the reduction in protein level of MGL as analyzed with Western blotting (FIG. 10C).

Figure 11A:
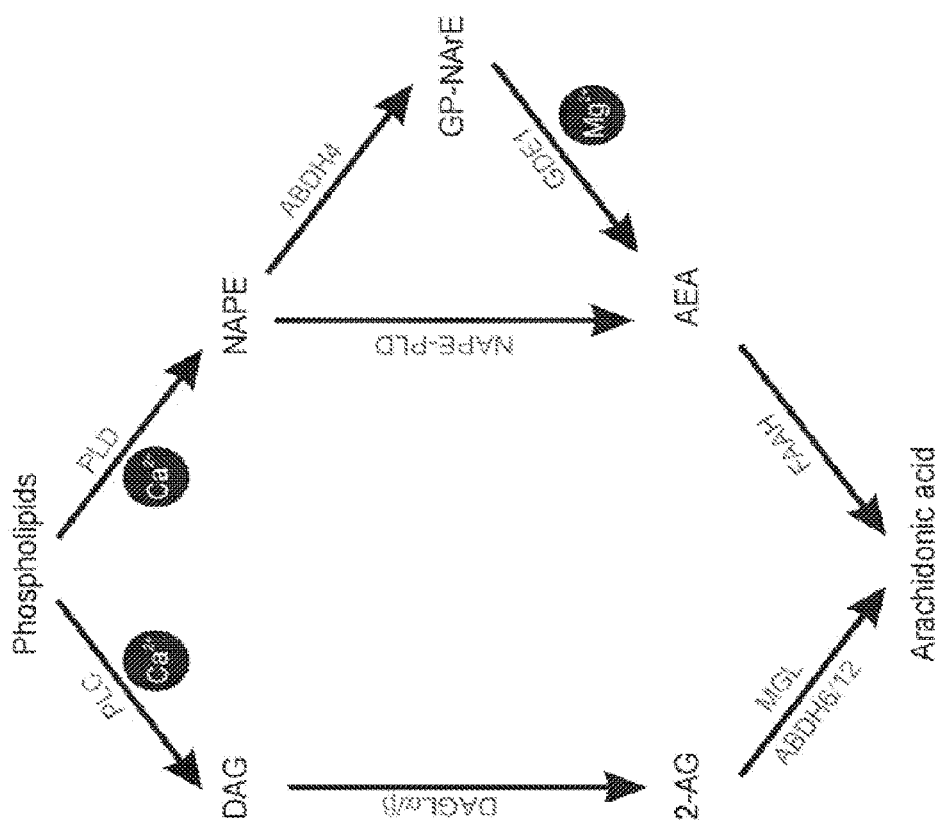

A scheme of synthesis and degradative enzymes of the endocannabinoid system is shown in FIG. 11A (FIGS. 11A and 11B were published by Anavi-Goffer & Mulder, Chembiochem. 2009 10:1591-8).

II. Postnatal Induction of Schizophrenia (Days 3-15) Followed by Treatment of Adolescent Mice with Bcp (Postnatal Days 43-61) Methods PCP 5 mg/kg was administered by injection on PND 3, 5, 7, 10, 12, 13, 15 and 17. Body weight was measured at every injection between PND 3-17. The open field test was conducted on PND 16.

When the mice were adolescent (PND 43-61), BCP (5 mg/kg in a mixture of DMSO:Cremophor EL:saline 0.6:1: 18.4) was injected twice a week (on Sunday and Wednesday) for 3 weeks, a total of 6 injections. After the final BCP injection, mice were tested in the open field test (PND 63), Elevated Plus Maze test (PND 64), PPI test (PND 68) and behavior at the Phenotyper cage (PND 91). Mice were re-tested at adulthood on PND 104 (open field), PND 105 (Phenotyper) PND 106 (PPI).

Results

Body Weight

As seen in FIG. 13A, PCP significantly reduced body weight in male and female mice as measured on days 3, 5, 7, 10, 12, 15 and 17.

Injections of BCP (5 mg/kg) on PND 43-61 did not affect body weight (FIG. 14A). At age PND 63 there was no significant difference in the body weight between vehicle-treated mice and PCP-treated mice (FIG. 14B).

Ambulation, Rearing

At PND 16, PCP significantly inhibited ambulation, rearing behaviors (FIGS. 13B, 13C).

BCP treatment during adolescence significantly reversed the effect of PCP on ambulation in male and female mice at PND 63 (FIGS. 14C-14E). BCP treatment in adolescence significantly inhibited the exploration of mice compared with saline-treated mice. BCP reversed the effect of PCP on rearing in both females and males (FIGS. 15A-15C).

Figure 23B:
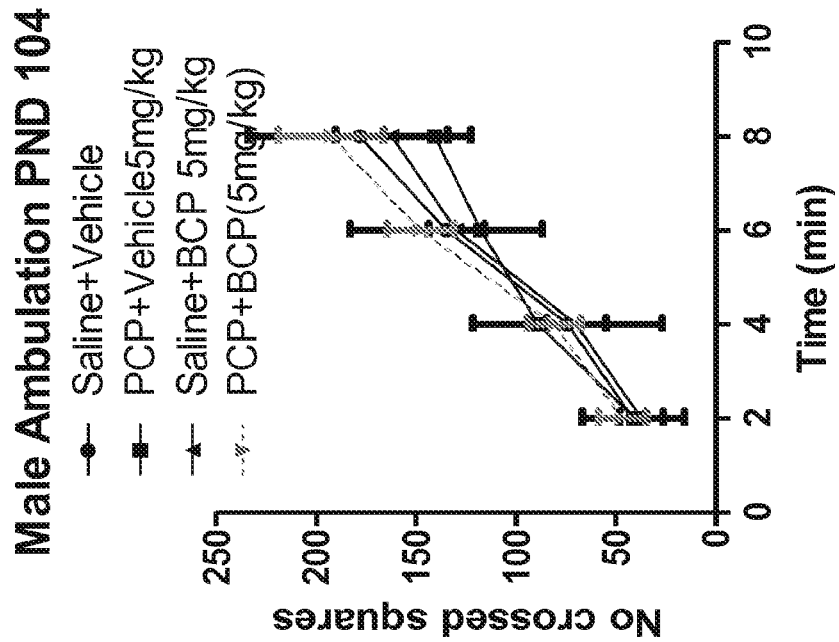
FIGS. 23A-23E show results demonstrating that BCP treatment at adolesence improved exploration and rearing behaviors of male PCP treated mice at PND 104: line graph of female ambulation at PND 104 (23A), line graph of male ambulation at PND 104 (23B), line graph of female rearing at PND 104 (23C), line graph of male rearing at PND 104 (23D) and line graph of male and female body weight at PND 104 (23E)
Figure 23A:
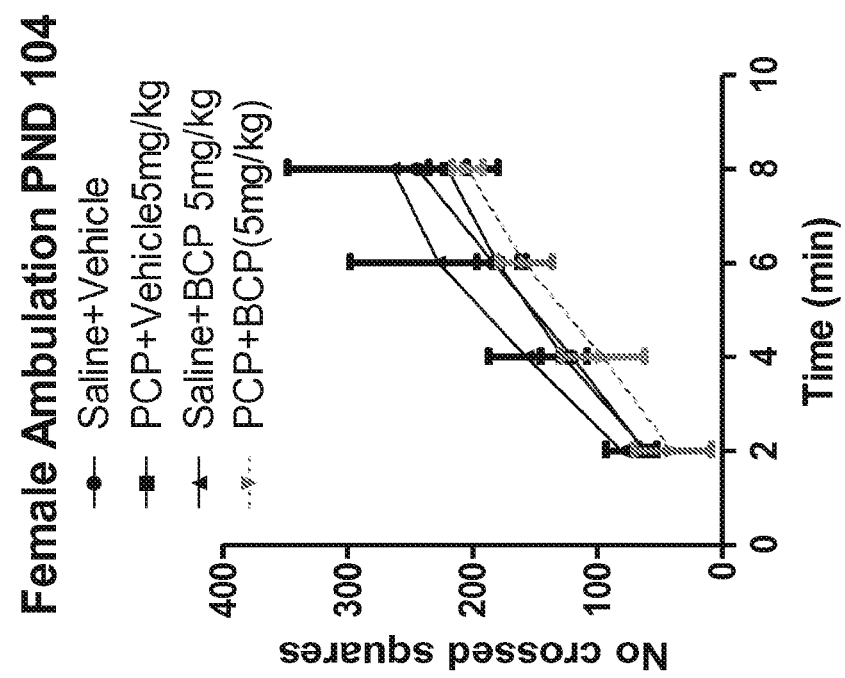
Figure 23C:
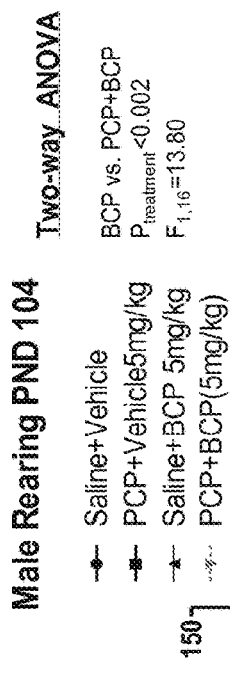
Figure 23E:
Figure 23D:
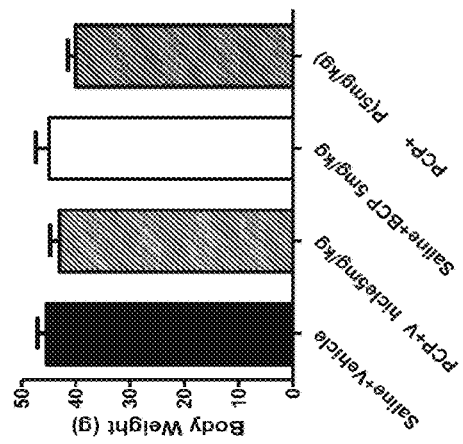
Figures 24A, 24B, 24C:
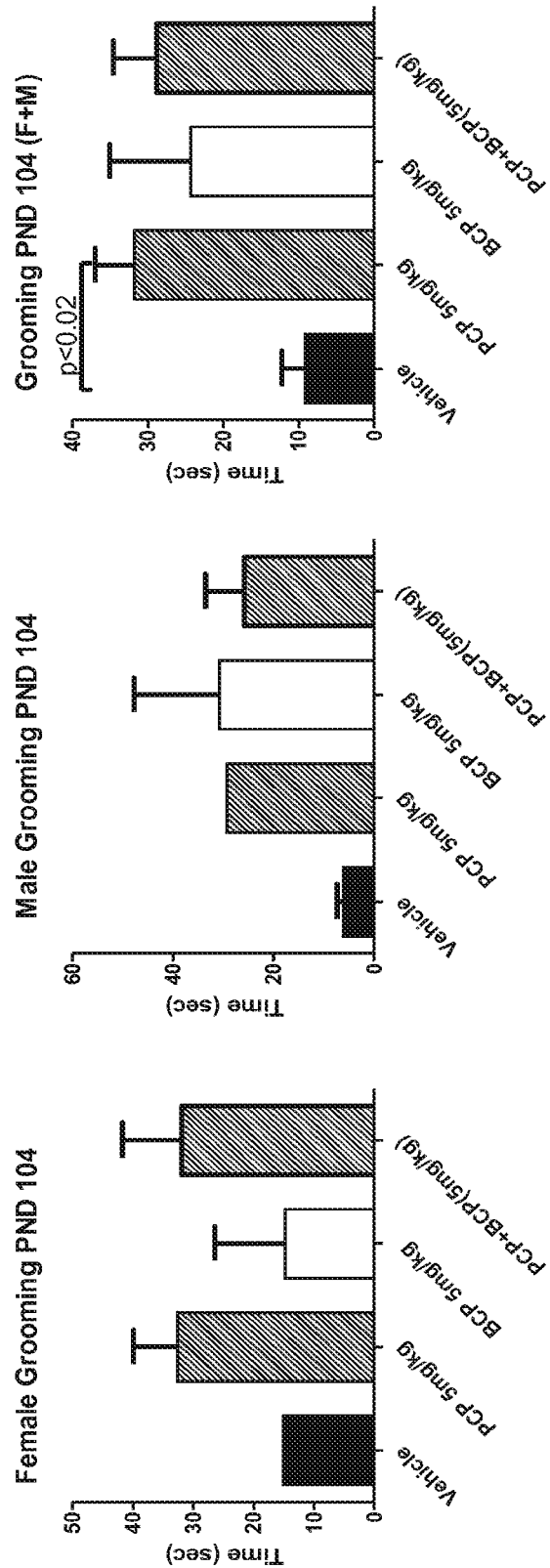
FIGS. 24A-24C show results demonstrating that BCP treatment at adolesence did not reverse the effect of PCT on grooming at PND104: bar graph of female grooming at PND 104 (24A), bar graph of male grooming at PND 104 (24B) and bar graph of male and female grooming at PND 104 (24C)

On PND 104 a relapse in exploratory behavior was evident in the schizophrenic female mice that had been treated with BCP (last BCP treatment was on PND 61), as seen in FIGS. 23A, 23C. Rearing behavior of male PCP-treated mice that had been treated with BCP was still significantly higher than that of PCP-treated mice with no BCP treatment (FIGS. 24B, 24C). There was no difference in body weight between groups (FIG. 24E). BCP treatment did not increase body weight in females and males, rather reduced body weight of PCP+BCP treated group (vehicle vs. PCP+BCP, P=0.06).

BCP treatment in adolescence did not reverse the effect of PCP on self-grooming (total, without stimuli) in females or males at PND 104 (FIGS. 24A, 24B, 24C).

Prepulse Inhibition and Startle Response

BCP treatment in adolescence significantly reversed the effect of PCP on pre-pulse inhibition (FIG. 16A). BCP had no substantial effect on saline-treated mice. BCP treatment at adolescent significantly reversed the effect of PCP on startle response in females (FIG. 16B). In males, there was no difference in the response to the startle stimuli between groups (FIG. 16C).

BCP treatment at adolescence significantly reversed the effect of PCP on response to pre-pulse tones (FIGS. 17A-17C). BCP had no effect on saline-treated mice.

Figure 18C:
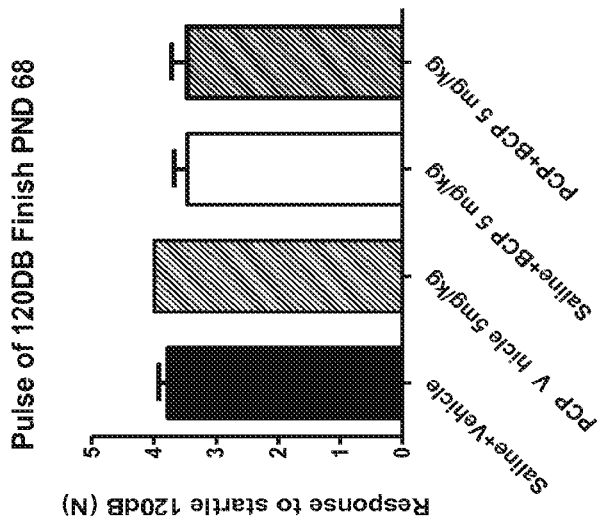
FIGS. 18A-18C show results demonstrating that BCP treatment at adolesence did not affect the startle response at the end of the PPI test: female startle response at PND 68 (18A), male startle response at PND 68 (18B) and all-mice startle response at PND68 (18C)
Figure 18B:
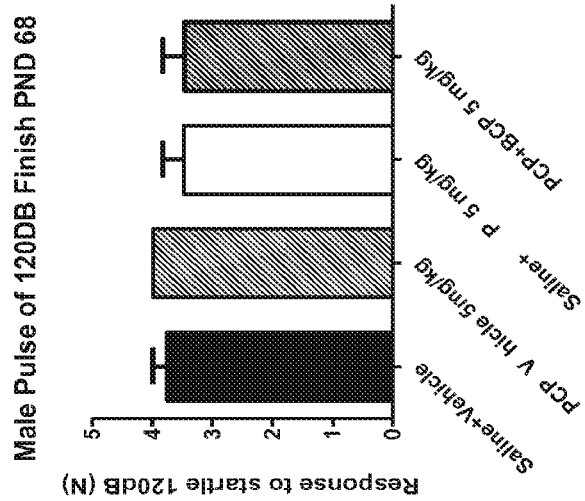
Figure 18A:
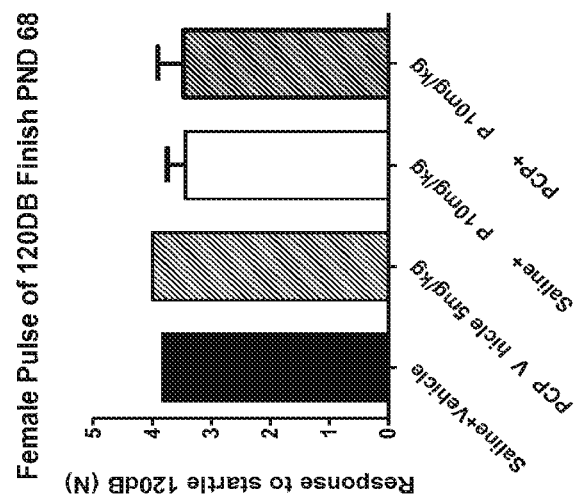

There was no difference between groups in the response to the startle stimuli at the end of the PPI test (FIGS. 18A-18C). BCP treatment at adolescence did not affect the response to startle at the end of the PPI test (FIGS. 18A-18C).

Figures 25G, 25H, 25I:
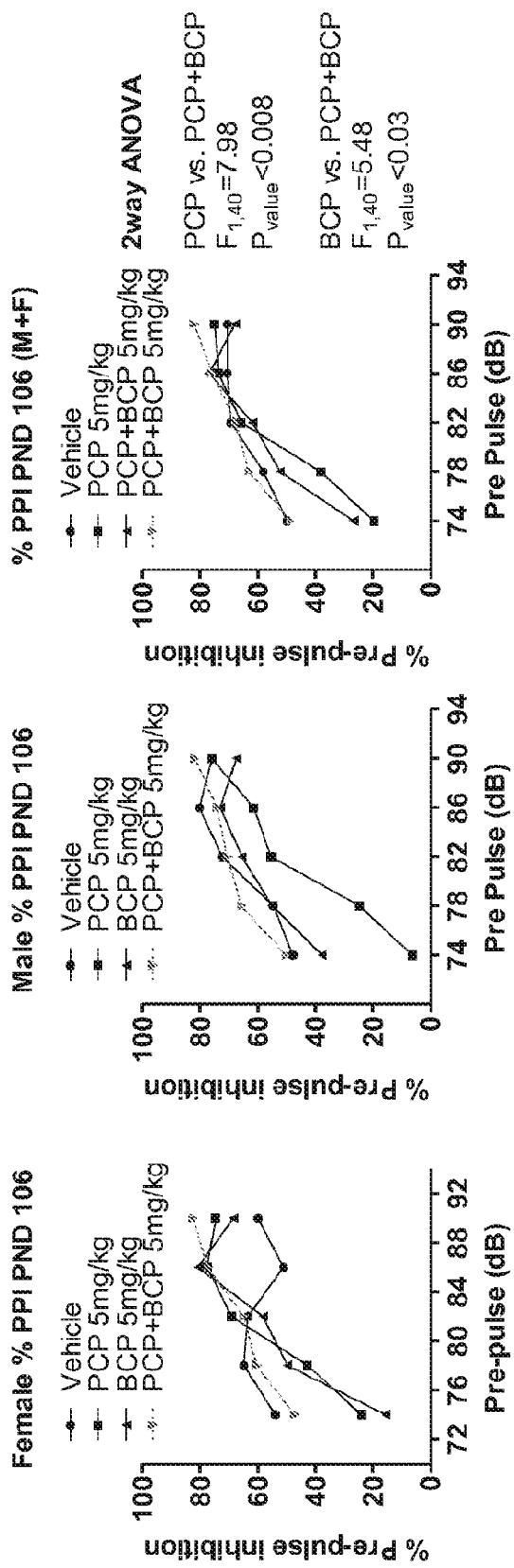

At PND 106, there was no difference in the response to the startle stimuli (120 dB) between groups (FIGS. 25A-25C). BCP reversed the effect of PCP on the response to tones (FIGS. 25D-25F). BCP treatment at adolescence reversed the effect of PCP on the % pre-pulse inhibition (PPI) (FIGS. 25G-25I).

Plus-Maze Test

BCP treatment at adolescence did not reverse the effects of PCP on behavior in the Plus Maze test at age 64 days (6 weeks) (FIGS. 19A-19F).

PhenoTyper Test

At PND 91, PCP increased the time spend at the Hidden Zone, indicating the PCP-treated mice had higher level of anxiety of mice at the PhenoTyper cage compared with vehicle-treated mice. BCP treatment at adolescence reversed the effects of PCP on the time spend in the Hidden Zone of PhenoTyper cage in females and males, respectively (FIGS. 20A, 20B). FIG. 20C shows combined results, suggesting that BCP reversed the effect of PCP on anxiety level. PCP appeared to reduce the frequency of entries to the Hidden Zone in males (FIG. 20D) but not in females (FIG. 20E). BCP reversed the effect of PCP in males (FIG. 20D).

Figure 21C:
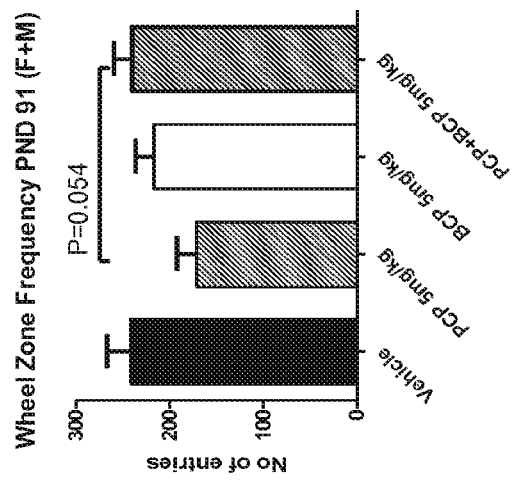
FIGS. 21A-21C show results demonstrating that BCP treatment at adolesence reversed the effects of PCP on frequency of entries to the wheel (motor behavior in the Phenotyper cage: bar graph of female wheel zone frequency at PND 91 (21A), bar graph of male wheel zone frequency at PND 91 (21B) and bar graph of male and female wheel zone frequency at PND 91 (21C)
Figure 21B:
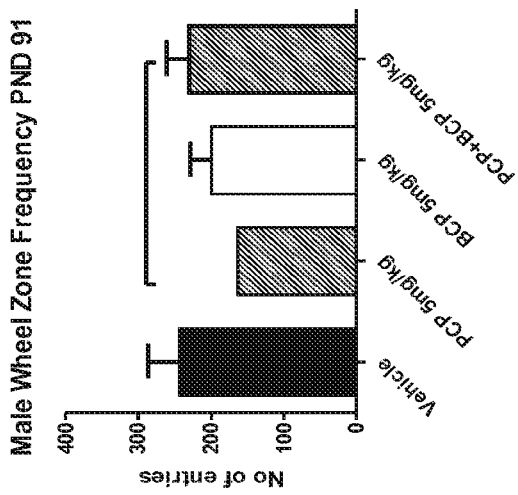
Figure 21A:
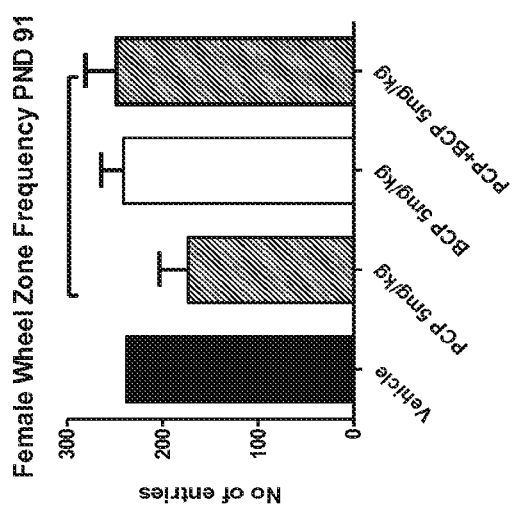

PCP reduced the frequency of entries to the wheel. BCP treatment at adolescence reversed the effects of PCP on the frequency of entries to the wheel in the Phenotyper cage both in females and males (FIGS. 21A, 21B). FIG. 21C, shows combined results of both sex. These results indicate that BCP reversed the action of PCP on loco/motor behavior.

BCP treatment at adolescence did not affect the time spend in the food zone (FIGS. 22A, 22B, 22C).

Compared with PCP-treated group, BCP treatment at adolescence appeared to reduce the time spend at the drinking zone (FIGS. 22D, 22E, 22F).

At PND 105, PCP increased the frequency of entries to the Hidden Zone, indicating an increased level of anxiety.

Figure 26A:
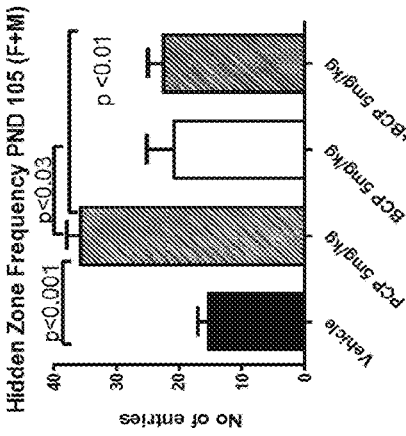
FIGS. 26A-26F show results demonstrating that BCP treatment at adolesence reversed the effect of PCP on frequency of entries to hidden zone (Phenotyper cage) at PND 105: bar graph of male hidden zone frequency at PND 105 (26A), bar graph of female hidden zone frequency at PND 105 (26B), bar graph of male and female hidden zone frequency at PND 105 (26C), bar graph of male wheel zone frequency at PND 105 (26D), bar graph of female wheel zone frequency at PND 105 (26E) and bar graph of male and female wheel zone frequency at PND 105 (26F)
Figure 26B:
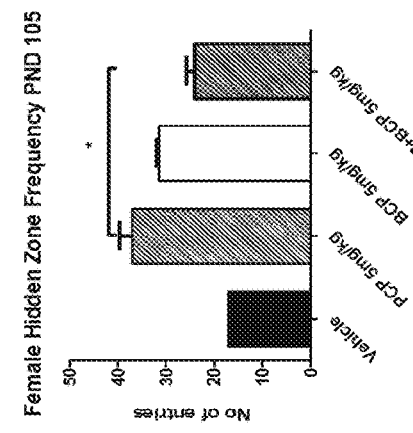
Figure 26C:
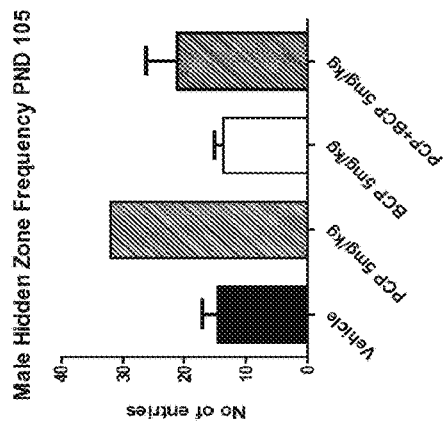
Figure 26D:
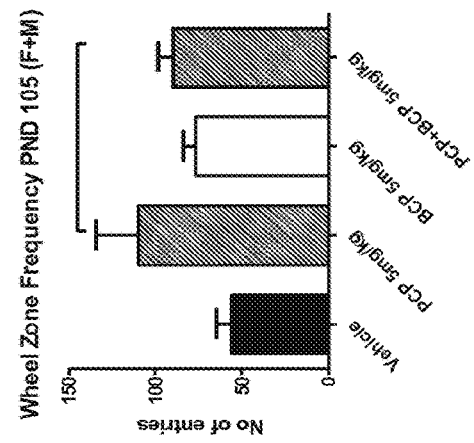
Figure 26E:
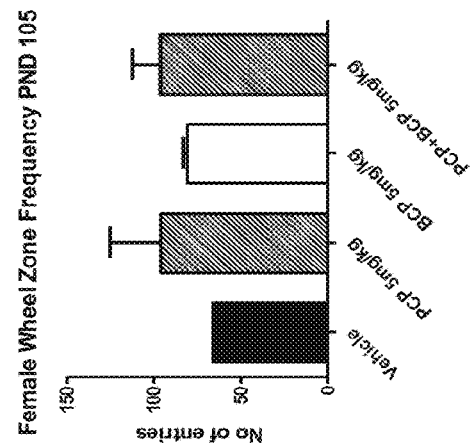
Figure 26F:
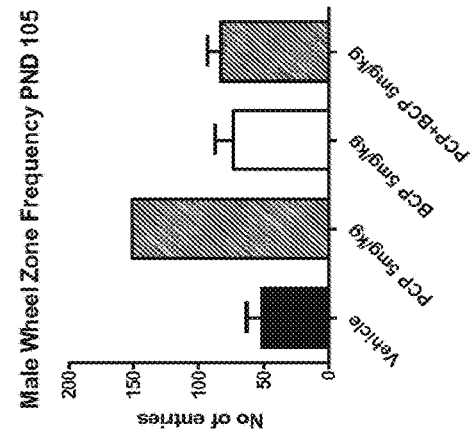

BCP treatment at adolescence reversed the effects of PCP on the frequency of entries to the hidden zone (FIGS. 26A, 26B, 26C). These results suggest that treatment with BCP reduced the level of stress and anxiety. BCP treatment appeared to reduce the effect of PCP on the frequency of entries to the Wheel Zone FIG. 26. This effect was prominent in males than in females (FIGS. 26D, 26E).

Figure 27A:
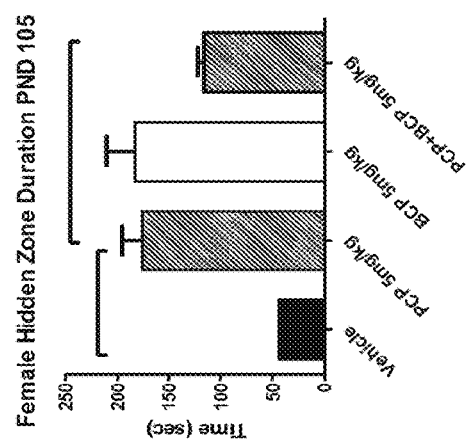
FIGS. 27A-27E show results demonstrating that BCP treatment at adolesence reversed the effect of PCP on time spent at the hidden zone but not the time spent in the wheel zone (Phenotyper cage) at PND 105: bar graph of male hidden zone duration at PND 105 (27A), bar graph of female hidden zone duration at PND 105 (27B), bar graph of male wheel zone duration at PND 105 (27C), bar graph of female wheel zone duration at PND 105 (27D) and bar graph of male and female wheel zone duration at PND 105 (27E)
Figure 27C:
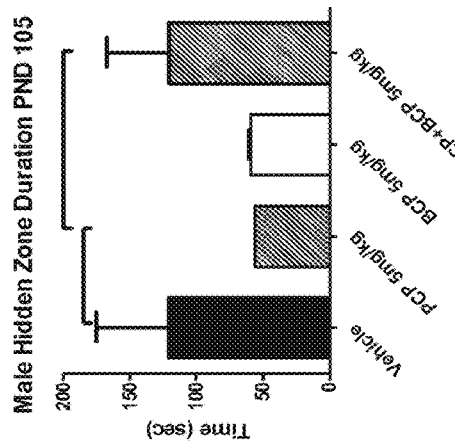
Figure 27B:
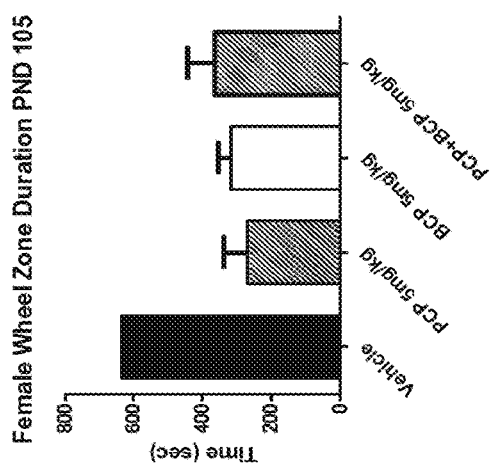
Figure 27D:
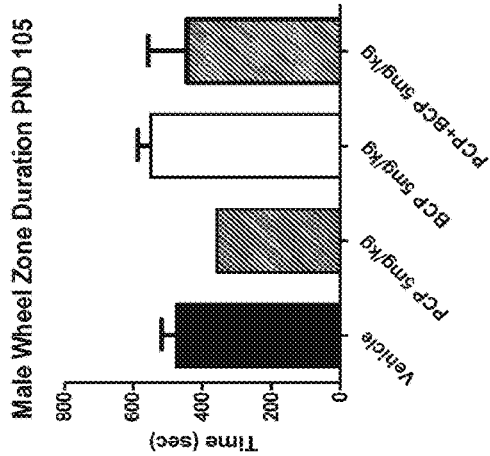
Figure 27E:
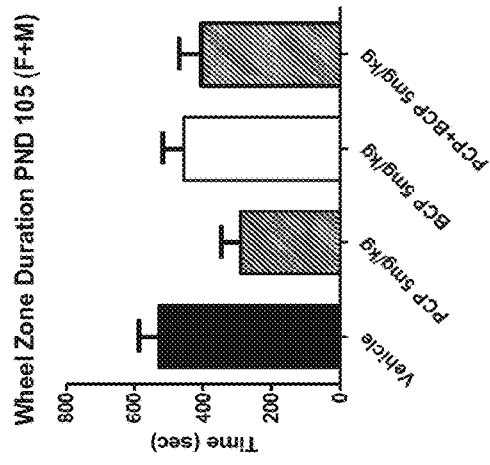
Figures 28A, 28B:
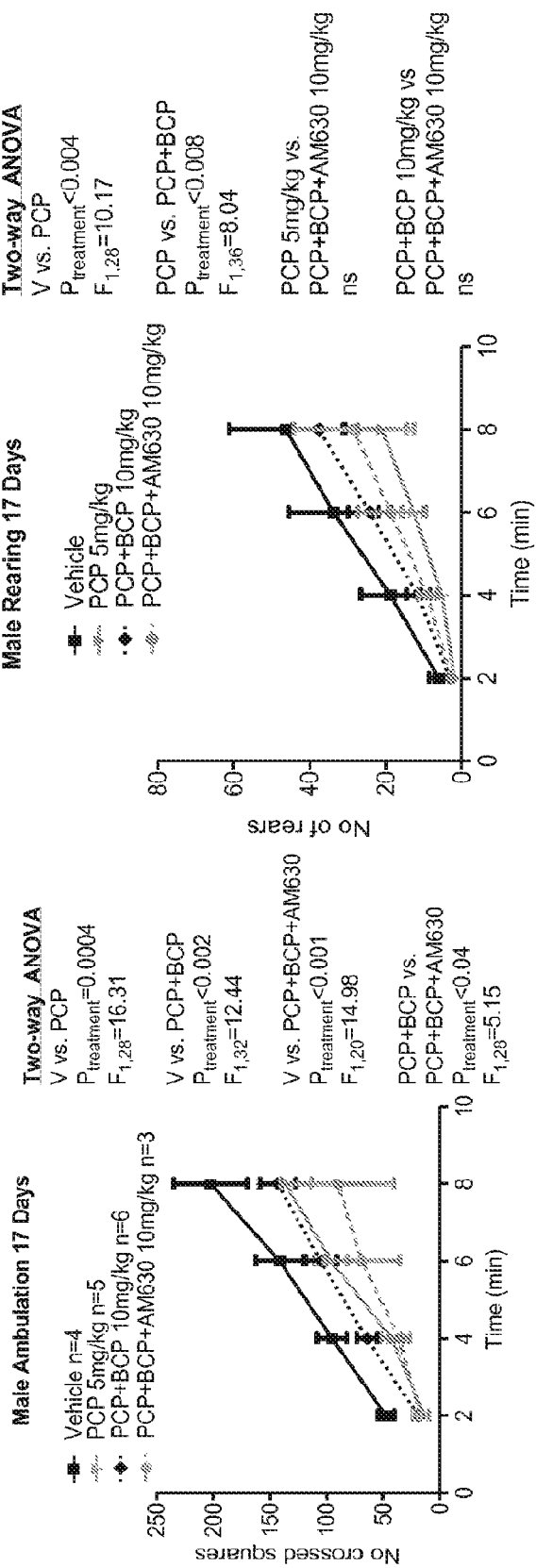
FIGS. 28A-28B show results demonstrating that AM630 reversed the effect of BCP on PCP-induced inhibition of ambulation and rearing: line graph of male ambulation at 17 days (28A) and line graph of male rearing at 17 days (28B).

At PND 105, BCP treatment at adolescence reversed the effects of PCP on the time spend at the hidden zone (FIGS. 27A, 27B). These results suggest that treatment with BCP reduced the level of stress and anxiety. BCP treatment at adolescence showed a trend to reverse the effect of PCP on the time spend in the wheel (FIGS. 27C, 27D, 27E).

III. Effects of AM630 (6-Iodopravadoline)

AM630 (6-Iodopravadoline, CAS 164178-33-0) is a molecule that acts as a potent and selective inverse agonist for the cannabinoid receptor CB2, with a Ki of 32.1 nM at CB2 and 165× selectivity over CB1, at which it acted as a weak partial agonist. It is used in the study of CB2 mediated responses.

Materials and Methods

Murine Model of Schizophrenia:

Mice were injected with PCP (5 mg/kg in saline) at postnatal days PND 4, 6, 8, 11, 13, 15, and 18 to provide a murine model of schizophrenia. A control group was injected with vehicle (0.6:1:18.4 DMSO:Cremophor EL:saline) alone.

Each experiment was repeated twice. In each experiment, male mice were divided into 4 groups:

Group 1: vehicle (n=4 pups, 1+3 pups, respectively);
Group 2: PCP (n=5 pups, 2+3 pups, respectively);
Group 3: PCP+BCP (n=6 pups, 2+4, respectively); and
Group 4: PCP+BCP+AM630 (n=3 pups, 1+2 respectively).

Administration of BCP or BCP+AM630

The effect of co-administering AM630 with BCP was studied.

One hour after each injection with PCP, mice were injected with vehicle or BCP (final dose 10 mg/kg in 1:0.6:18 Cremophor EL:DMSO:saline) or BCP+AM630 (equal parts of 20 mg/kg BCP in DMSO and 20 mg/kg AM630 in DMSO, providing a final concentration of 10 mg/kg each of BCP and AM630, mixed together).

Results

Rearing and Exploration

At PND 17, locomotor activity, hyperactivity, exploratory and grooming behaviors were tested with the open-field test (FIGS. 29A and 29B). PCP significantly inhibited both ambulation and rearing behaviors. Treatment with BCP reversed the effects of PCP on rearing and exploration. AM630 reversed the effects of BCP on ambulation and rearing behaviors. The behaviors of mice that had been treated with AM630 were not significantly different from these of PCP-treated mice.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

REFERENCES

Anavi-Goffer, S., G. Baillie, A. J. Irving, J. Gertsch, I. R. Greig, R. G. Pertwee, and R. A. Ross. (2011) Modulation of L-alpha-lysophosphatidylinositol/GPR55 MAP kinase signalling by cannabinoids. *J Biol Chem.* 287: 91-104.

Ballmaier M, Bortolato M, Rizzetti C, Zoli M, Gessa G, Heinz A, Spano P. (2007) Cannabinoid receptor antagonists counteract sensorimotor gating deficits in the phencyclidine model of psychosis. Neuropsychopharmacology. 32: 2098-2107.

De Marchi N, De Petrocellis L, Orlando P, Daniele F, Fezza F, Di Marzo V (2003) Endocannabinoid signalling in the blood of patients with schizophrenia. Lipids Health Dis. 2:5.

Di Marzo V, Bifulco M, De Petrocellis L (2004) The endocannabinoid system and its therapeutic exploitation. Nat Rev Drug Discov. 3:771-784.

Fride E, Gobshtis N, Dahan H, Weller A, Giuffrida A, Ben-Shabat S (2009) The endocannabinoid system during development: emphasis on perinatal events and delayed effects. Vitam Horm. 81:139-58.

Gambi F, De Berardis D, Sepede G, Quartesan R, Calcagni E, Salerno R M, Conti C M, Ferro F M (2005) Cannabinoid receptors and their relationships with neuropsychiatric disorders. Int J Immunopathol Pharmacol. 18:9-25.

Gardner E L (2005) Endocannabinoid signaling system and brain reward: emphasis on dopamine. Pharmacol Biochem Behav. 81:263-284.

Gertsch J, et al. 2008. Beta-caryophyllene is a dietary cannabinoid. Proc Natl Acad Sci USA 105(26): 9099-9104.

Henstridge, C. M., N. A. Balenga, R. Schroder, J. K. Kargl, W. Platzer, L. Martini, S. Arthur, J. Penman, J. L. Whistler, E. Kostenis, M. Waldhoer, and A. J. Irving. (2010). GPR55 ligands promote receptor coupling to multiple signalling pathways. *Br J Pharmacol.* 160: 604-14.

Hashimoto K, Fujita Y, Shimizu E, Iyo M (2005) Phencyclidine-induced cognitive deficits in mice are improved by subsequent subchronic administration of clozapine, but not haloperidol. Eur J Pharmacol. 519: 114-117.

Josselyn S A and Vaccarino F J (1998) Preclinical behavioral approaches and study of antipsychotic drug action and schizophrenia, in in vivo neuromethods (Boulton A A, Baker G B and Bateson A N eds) pp 177-225, Humana Press, Totowa.

Leweke F M, Giuffrida A, Wurster U, Emrich H M, Piomelli D (1999) Elevated endogenous cannabinoids in schizophrenia. Neuroreport. 10:1665-1669.

Long L E, Malone D T, Taylor D A. (2006) Cannabidiol reverses MK-801-induced disruption of prepulse inhibition in mice. Neuropsychopharmacology. 4: 795-803.

Newell K A, Deng C, Huang X F. (2006) Increased cannabinoid receptor density in the posterior cingulate cortex in schizophrenia. Exp Brain Res. 172:556-60.

Ortega-Alvaro, A., A. Aracil-Femandez, M. S. Garcia-Gutierrez, F. Navarrete, and J. Manzanares. (2011) Deletion of CB2 cannabinoid receptor induces schizophrenia-related behaviors in mice. Neuropsychopharmacology 36:1489.

Takahashi M, Kakita A, Futamura T, Watanabe Y, Mizuno M, Sakimura K, Castren E, Nabeshima T, Someya T, Nawa H (2006) Sustained brain-derived neurotrophic factor up-regulation and sensorimotor gating abnormality induced by postnatal exposure to phencyclidine: comparison with adult treatment. J Neurochem. 99:770-780.

Turgeon S M, Kim D, Pritchard M, Salgado 5, Thaler A (2011) The effects of phenylcyclidine (PCP) on anxiety-like behavior in the elevated plus maze and the light-dark exploration test are age dependent, sexually dimorphic and task dependent.

Varty G B, Walters N, Cohen-Williams M, Carey G J (2001) Comparison of apomorphine, amphetamine and dizocilpine disruptions of prepulse inhibition in inbred and outbred mice strains. Eur J Pharmacol. 424:27-36.

Wang C Z & Johnson K M (2005) Differential effects of acute and subchronic administration on phencyclidine-induced neurodegeneration in the perinatal rat. J Neurosci Res. 81:284-292.

Wiley J L, Cristello A F, Balster R L (1995) Effects of site-selective NMDA receptor antagonists in an elevated plus-maze model of anxiety in mice. Eur J Pharmaco. 294: 101-107

The invention claimed is:

1. A method for treating schizophrenia in a subject in need thereof, the method comprising administering a therapeutic composition comprising beta-caryophyllene (BCP) and a pharmaceutically effective carrier.

2. The method of claim 1, wherein said schizophrenia is selected from the group consisting of paranoid schizophrenia; disorganized schizophrenia; undifferentiated schizophrenia; catatonic schizophrenia; and residual schizophrenia.

3. The method of claim 1, wherein said treating comprises treating at least one symptom of schizophrenia selected from the group consisting of a negative symptom of schizophrenia and a positive symptom of schizophrenia.

4. The method of claim 1, wherein an average daily amount of said BCP administered is from about 0.4 mg/kg to about 2 mg/kg.

5. The method of claim 1, wherein said pharmaceutically effective carrier comprises dimethyl sulfoxide (DMSO).

6. The method of claim 1, wherein said administering comprises injecting said composition to said subject.

7. The method of claim 1, wherein said administering comprises orally administering said composition to said subject.

8. The method of claim 1, further comprising co-administering at least one additional antipsychotic agent.

9. The method of claim 8, wherein said at least one additional antipsychotic agent is chlorpromazine, haloperidol, perphenazine, fluphenazine, clozapine, risperidone, olanzapine, quetiapine, ziprasidone, aripiprazole, paliperidone, or combinations thereof.

10. The method of claim 8, wherein said at least one additional antipsychotic agent is co-administered in a single dosage form together with said BCP or in dosage from separate from said BCP.

* * * * *